(12) United States Patent
McCord et al.

(10) Patent No.: US 10,383,606 B1
(45) Date of Patent: Aug. 20, 2019

(54) TOILET BASED URINE ANALYSIS SYSTEM

(71) Applicant: Bloom Health, Inc., San Diego, CA (US)

(72) Inventors: Matthew McCord, San Diego, CA (US); Jon Carder, San Diego, CA (US); Sergio Alvarez, San Diego, CA (US); Jesus Gonzalez, San Diego, CA (US)

(73) Assignee: BLOOM HEALTH, INC., San Diego, CA (US)

( * ) Notice: Subject to any disclaimer, the term of this patent is extended or adjusted under 35 U.S.C. 154(b) by 0 days.

(21) Appl. No.: 16/036,621

(22) Filed: Jul. 16, 2018

(51) Int. Cl.
*A61B 10/00* (2006.01)
*G01N 33/52* (2006.01)
*G01N 1/20* (2006.01)
*E03D 11/13* (2006.01)
*G01N 33/543* (2006.01)
(Continued)

(52) U.S. Cl.
CPC .......... *A61B 10/007* (2013.01); *A61B 5/486* (2013.01); *E03D 11/13* (2013.01); *G01N 1/2035* (2013.01); *G01N 33/493* (2013.01); *G01N 33/528* (2013.01); *G01N 33/54386* (2013.01); *C12Q 1/006* (2013.01); *C12Q 1/54* (2013.01); *G08C 17/02* (2013.01)

(58) Field of Classification Search
CPC .......... A61B 10/007; A61B 10/0038; A61B 5/14532; A61B 5/14546; C12Q 1/54; C12Q 1/006; Y10S 435/97; G01N 33/493; G01N 33/528; E03D 9/00; E03D 11/00; Y10T 436/118339; Y10T 436/25
See application file for complete search history.

(56) References Cited

U.S. PATENT DOCUMENTS 4,218,421 A * 8/1980 Mack, Jr. ............... G01N 31/22
422/561
5,184,359 A * 2/1993 Tsukamura ........ A61B 5/02241
4/314
(Continued)

FOREIGN PATENT DOCUMENTS

WO   WO 2017/027994 A1 *  2/2017

OTHER PUBLICATIONS

Machine translation of WO 2017/027994 A1.*
(Continued)

*Primary Examiner* — David J. McCrosky
(74) *Attorney, Agent, or Firm* — Arc IP Law, PC; Joseph J. Mayo

(57) ABSTRACT

Urine analysis system that couples or integrates with a toilet. Wirelessly links to a computer, such as a user's mobile device to accept control inputs and report urine test results. Accepts user input to initiate testing and deploys a urine collector into the toilet bowl above the water to collect a urine sample. The collected urine sample is dispensed onto multiple regions of a test matrix that may perform many urine tests simultaneously. A single test matrix may include multiple types of tests, such as immunochromatography and colorimetric assays. An optical imaging system detects reaction of the urine with reagents integrated into the test matrix. Analysis of images may be performed locally or on a remote server. The system may store an inventory of test matrices to support daily testing for long durations, for example 6 months or more before refilling.

26 Claims, 18 Drawing Sheets

(51) Int. Cl.
*G01N 33/493* (2006.01)
*A61B 5/00* (2006.01)
*G08C 17/02* (2006.01)
*C12Q 1/54* (2006.01)
*C12Q 1/00* (2006.01)

(56) References Cited

U.S. PATENT DOCUMENTS

| | | | | |
|---|---|---|---|---|
| 5,720,054 | A * | 2/1998 | Nakayama | A61B 10/007 4/420 |
| 6,295,506 | B1 * | 9/2001 | Heinonen | A61B 5/14532 702/104 |
| 6,572,564 | B2 * | 6/2003 | Ito | A61B 5/0002 4/314 |
| 6,977,722 | B2 * | 12/2005 | Wohlstadter | B01L 3/5085 356/246 |
| 7,148,070 | B2 * | 12/2006 | Minter | A61B 10/007 436/169 |
| 2017/0022536 | A1 | 1/2017 | Velazquez et al. | |
| 2018/0184906 | A1 | 7/2018 | Prokopp | |

OTHER PUBLICATIONS

Cherkupally, et al. "Immobilized coupling reagents: Synthesis of amides/peptides." ACS combinatorial science16.11 (2014): Abstract. (Year: 2014).*

Investigación y Desarrollo. "New device measures glucose in urine, ending annoying needle pricks." ScienceDaily, retrieved from https://www.sciencedaily.com/releases/2015/11/151111172223.htm , published Nov. 11, 2015. (3 pages).

Grothaus, Sarah, "StreamSense Medical on the Potential of Biomarker Businesses to Create Big Impact", Vlab blog article retrieved from https://vlab.virginia.edu/ilab/b/news/posts/streamsense-medical-on-the-potential-of-biomarker-businesses-to-create-big-impact, published Jun. 29, 2017 (4 pages).

Kern, Theresa, "Digital Health Champions: Bringing Automated Healthcare Into Peoples' Homes", Digital Health Careers, article retrieved from https://digitalhealth.careers/digital-health-champions-medipee/#.W3XMoqknZT4, published Dec. 11, 2017 (10 pages).

Young, Clayton, "Tech in Japan: Take Your Toilet to the Cloud", article retrieved from https://www.kenkyoinvesting.com/2017/02/01/tech-in-japan-take-your-toilet-to-the-cloud/ , published Feb. 1, 2017 (11 pages).

Mitsuhashi, Yukari, "Japan's preventive healthcare startup Symax secures funding from Draper Nexus, others", article retrieved from http://thebridge.jp/en/2015/12/symax-fund-raising-november-2015 , published Dec. 9, 2015.

Piciocchi, Alice, "State-of-the-art bathroom", article retrieved from http://www.abitare.it/en/design-en/products/2017/08/07/high-tech-bathroom/ , published Aug. 7, 2017 (1 page).

"The Medic. Life Smart Toilet", Norima Consulting, web page retrieved from https://norimaconsulting.com/portfolio/the-medic-life-smart-toilet/ on Aug. 31, 2018, (5 pages).

Saenz, Aaron, "Smart Toilets: Doctors in Your Bathroom", Singularity Hub, article retrieved from https://singularityhub.com/2009/05/12/smart-toilets-doctors-in-your-bathroom/. May 12, 2009 (4 pages).

* cited by examiner

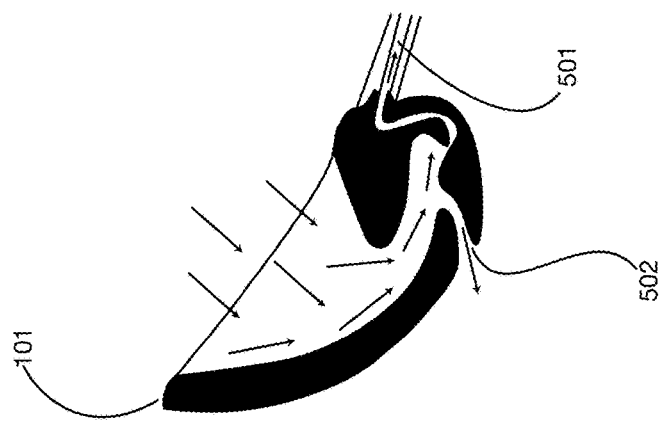
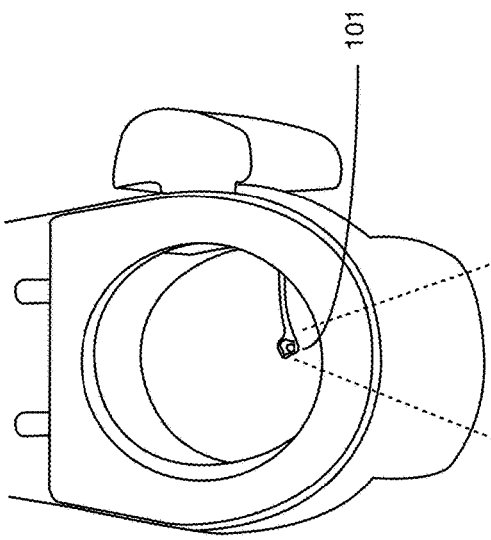
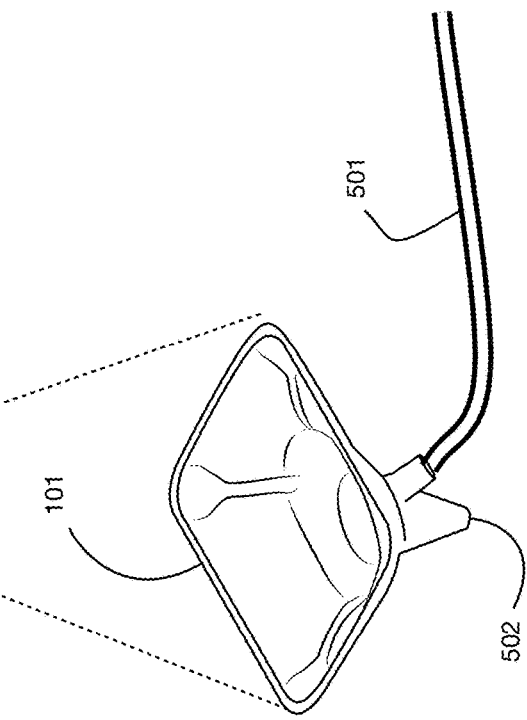

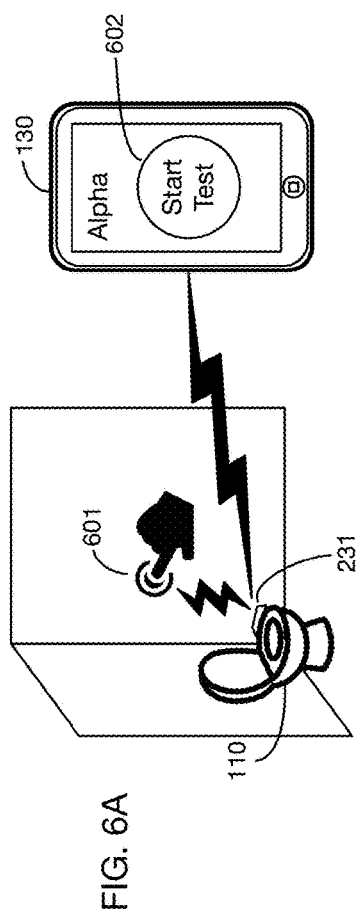
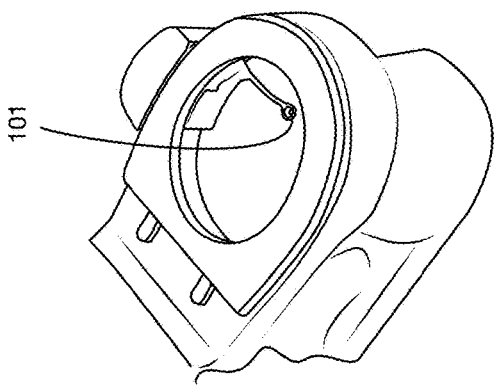
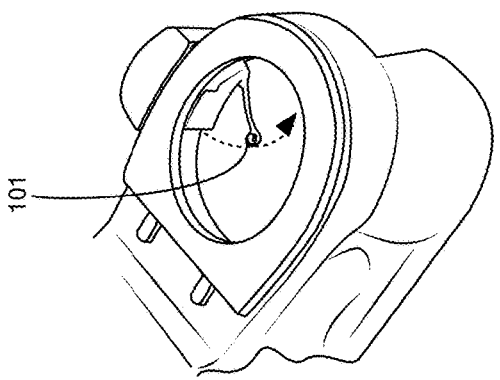
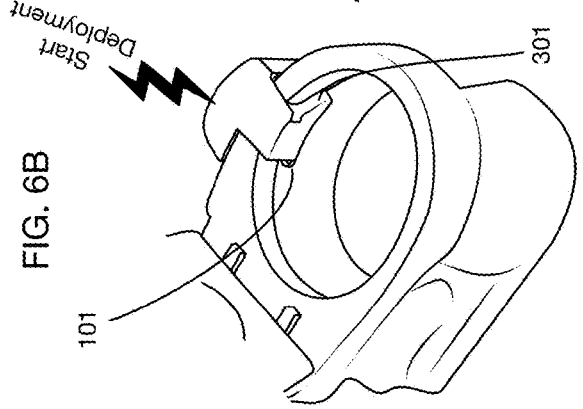
FIG. 6A
FIG. 6B
FIG. 6C
FIG. 6D

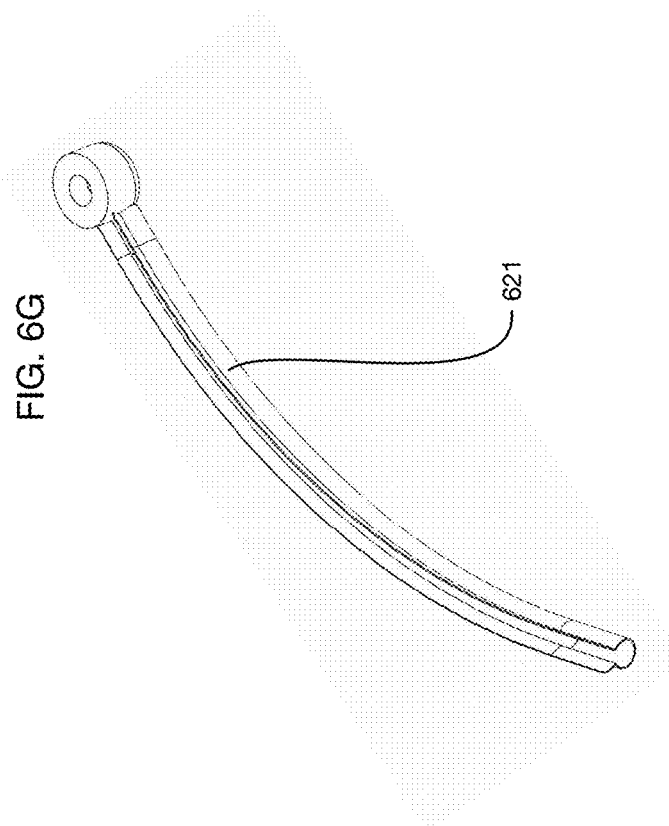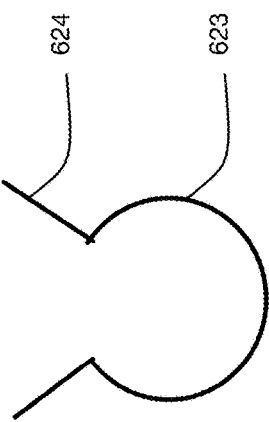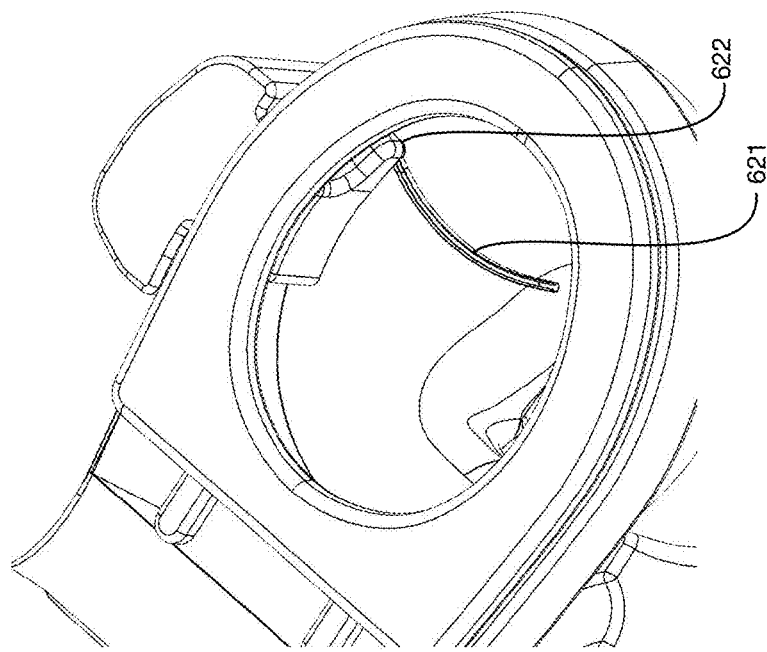

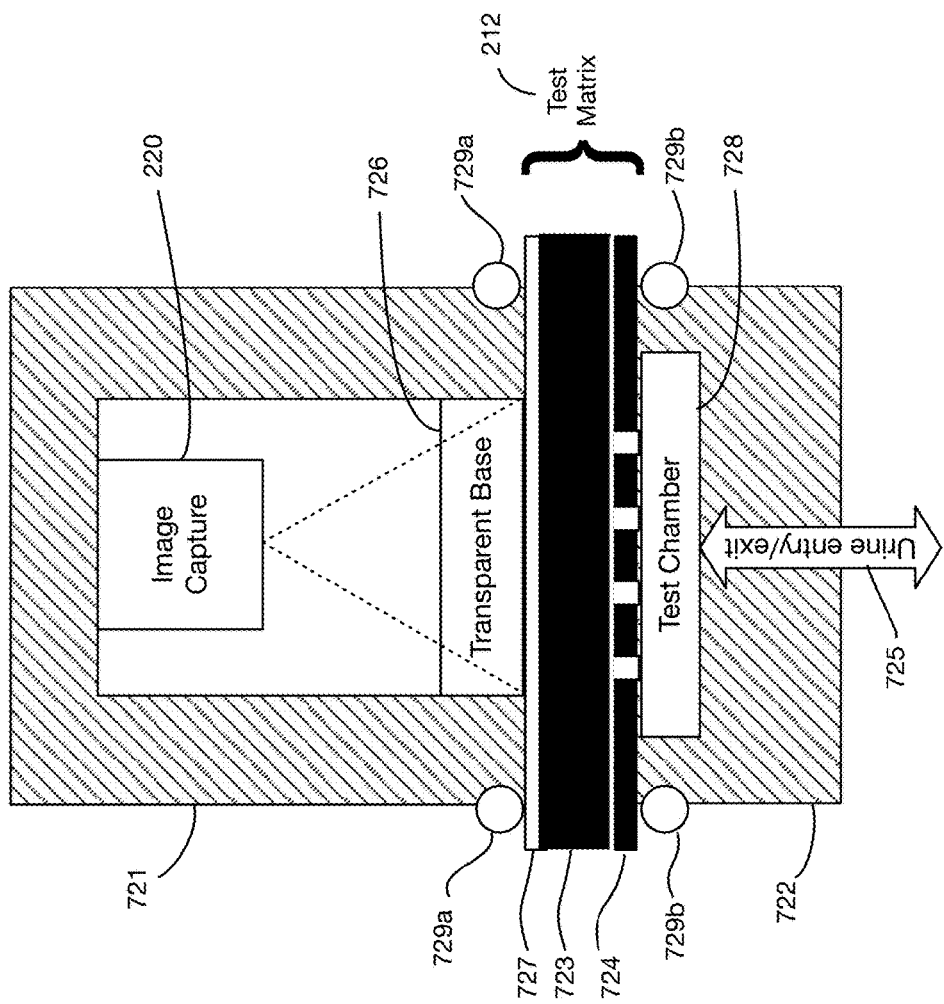

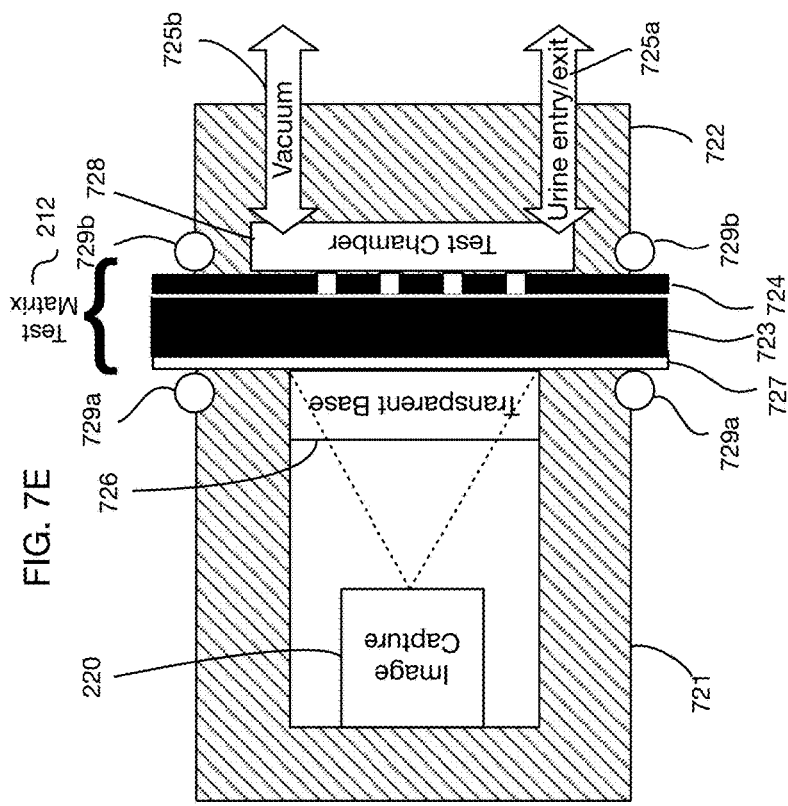
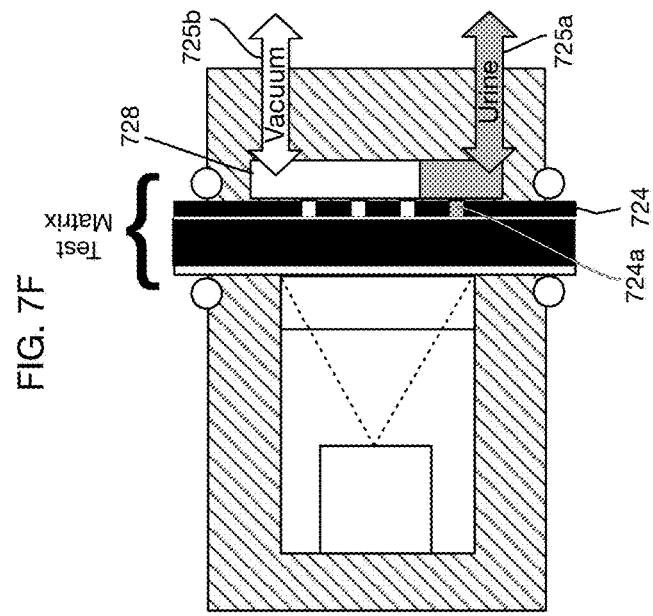

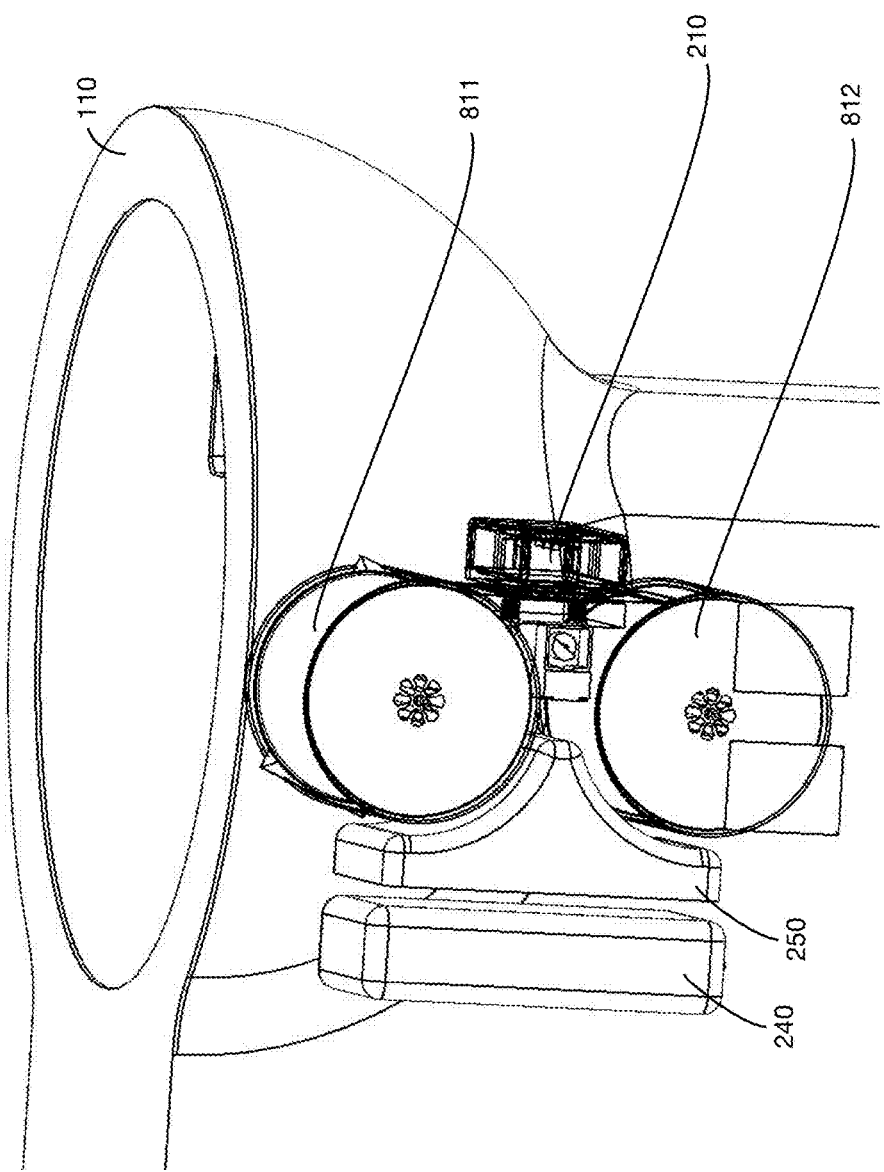

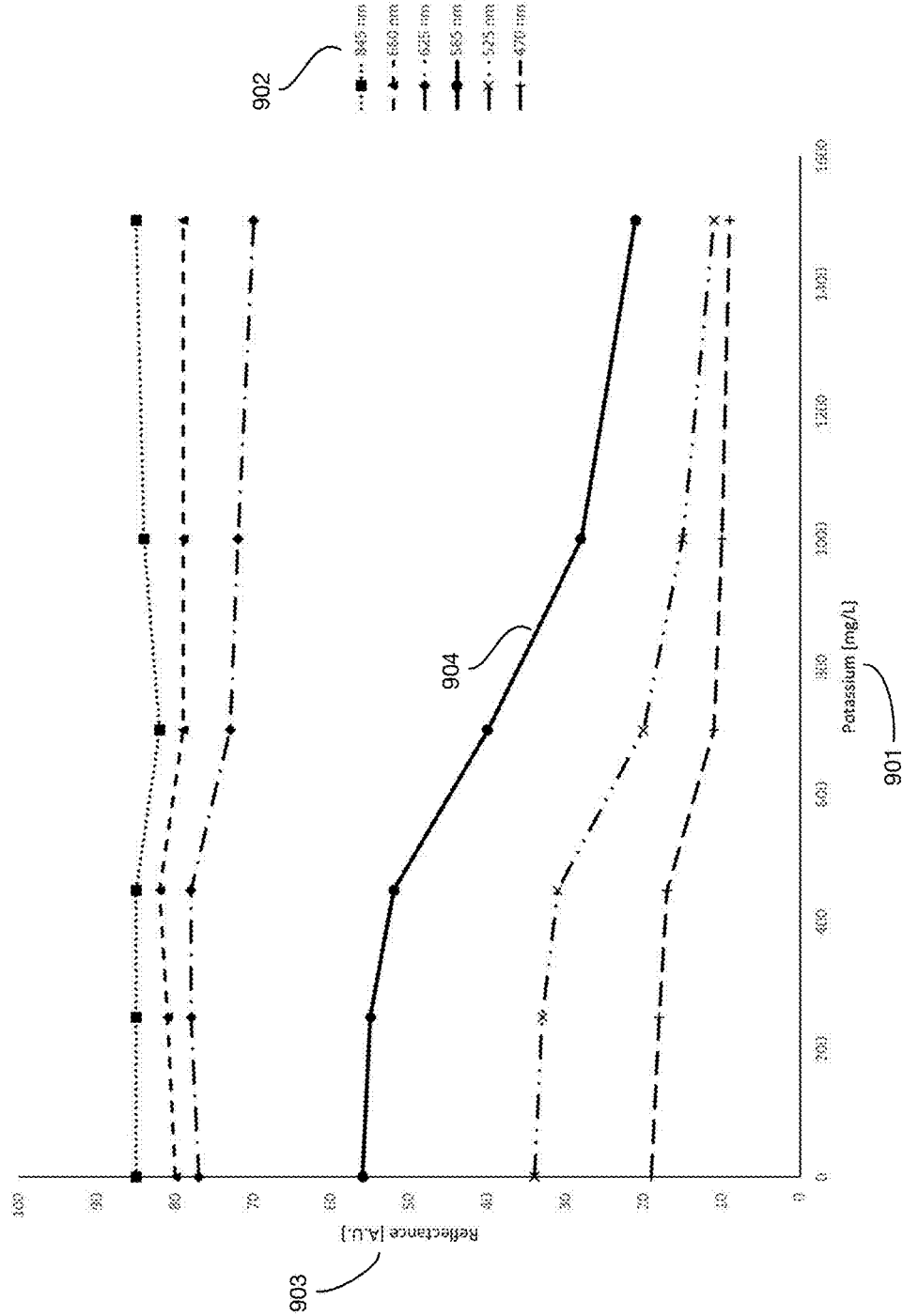

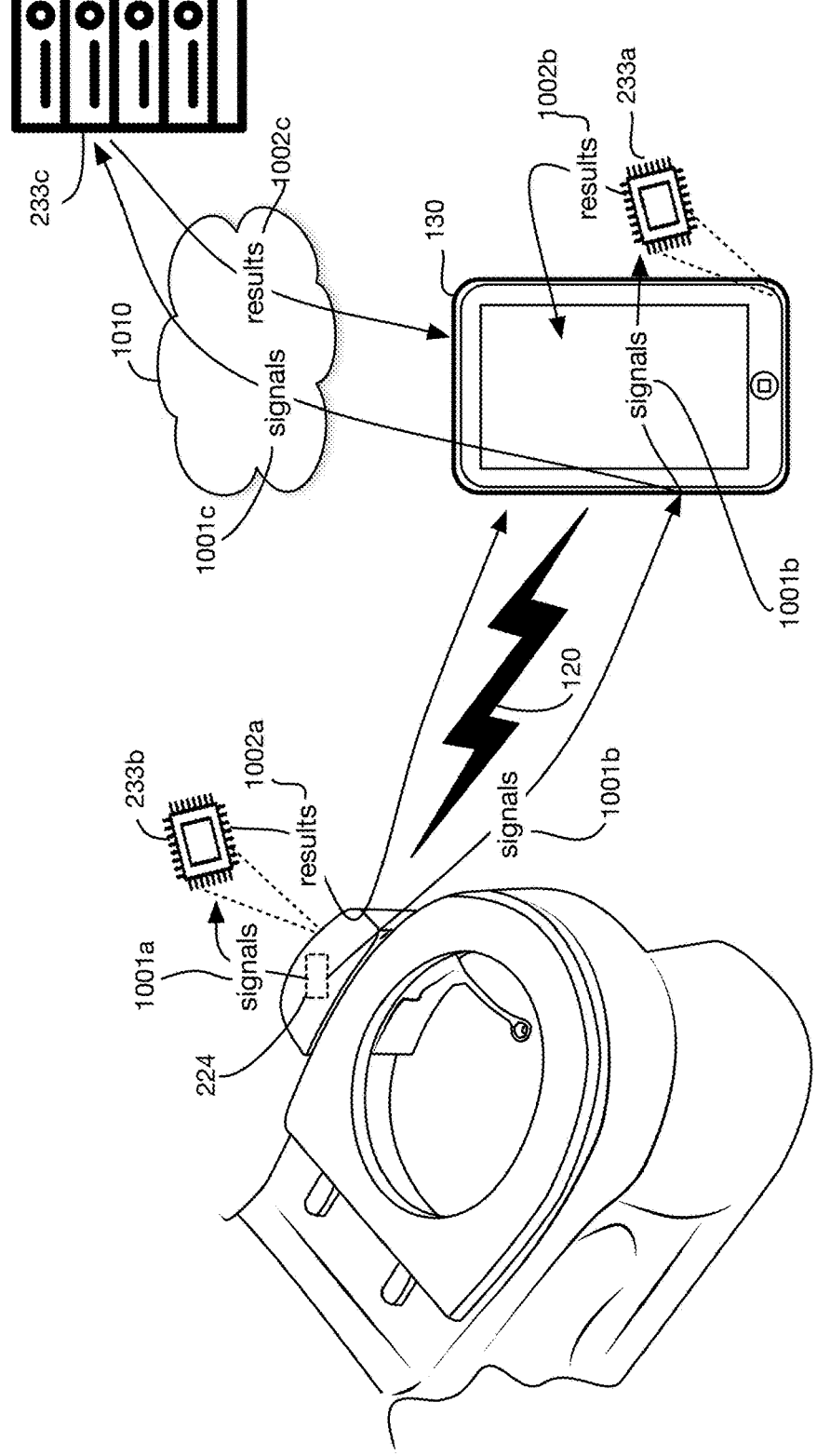

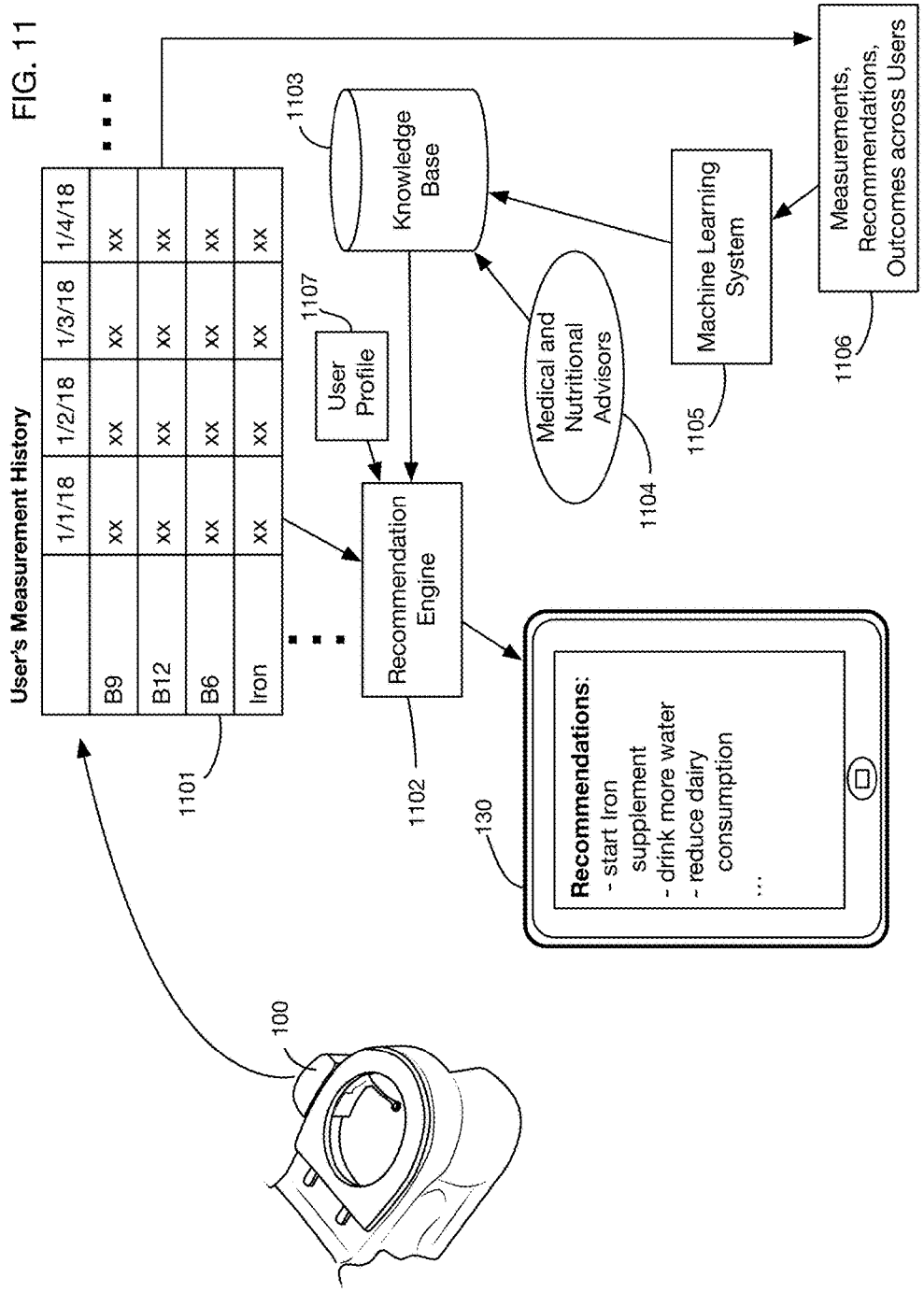

TOILET BASED URINE ANALYSIS SYSTEM

BACKGROUND OF THE INVENTION

Field of the Invention

One or more embodiments of the invention are related to the field of biochemical analysis of a body fluid, such as a urine or saliva sample, and are also related to mounting systems. More particularly, but not by way of limitation, one or more embodiments of the invention enable a urine sample collection and analysis system that may be mounted on a urinal collection apparatus, for example a toilet or urinal, while other embodiments may be mounted on a countertop or in any convenient location.

Description of the Related Art

Analysis of a person's body fluid, for example urine, currently requires the person to obtain a physician order, visit a laboratory to provide a urine sample, wait for the laboratory's specialized equipment and personnel to analyze the sample and then release the results to the person. This process is slow, inconvenient and expensive. Alternatively, a person may buy test strips and urinate on them, however this approach is highly unreliable due to lighting conditions, each person's color sensitivity, print fidelity of the color chart provided with the color strips, amount of urine used, time from urine exposure to when test is read, etc. As a consequence, urine is not routinely analyzed except for specific suspected or known medical conditions. In addition, urine analysis is generally limited to a small number of specific tests, because of the time and expense required to perform the analyses. Another disadvantage of urine analysis in a laboratory is that urine test results can vary significantly throughout the day; urine lab tests may therefore not produce reliable and repeatable measurements. Although labs sometimes do 24-hour urine tests in an attempt to compensate for within-day variation, this imposes an additional collection burden on the patient and is therefore not routinely performed. Moreover, it is impractical for a patient to visit a lab on a regular basis for urine analysis, so laboratory testing generally cannot monitor trends over time. In-home urine testing would overcome many of these limitations of laboratory urine testing. Although embodiments herein are described in terms of urine, other embodiments may be utilized for saliva.

Known systems that include urinalysis capabilities and that mount on toilets are generally limited in the number of substances that may be analyzed or have limits with respect to the number of samples or sensitivity of the analysis. Other limitations include lack of Internet or wireless functionality, associated remote monitoring capabilities, and full automation.

It is desirable to have a urine analysis system that can monitor a potentially large number of substances in urine on a regular basis. Ideally this analysis would be performed in the user's, or family's home, or in an office or other room associated with at least one user, obviating the need for trips to a laboratory or test orders from a physician. Attachment or integration of a urine analysis system into a home toilet, or toilet at any other location, in one embodiment for example would provide maximum convenience and would allow for analysis whenever the user urinates into the toilet, thus providing trends and consistent monitoring of analytes of interest. For at least the limitations described above there is a need for a toilet based urine analysis system that may for example include toilet mountable or toilet integrated housing or standalone housing, or for example be detached and relocated to another location.

BRIEF SUMMARY OF THE INVENTION

One or more embodiments described in the specification are related to a toilet based urine analysis system that may for example include toilet mountable or toilet integrated housing or standalone housing. One or more embodiments may include components that are attached to, integrated into, or proximal to a toilet or other apparatus that may be utilized to collect urine, such as a urinal, so that a urine sample may be collected directly during routine urination and analyzed immediately at the point of use. Thus, toilet for the purpose of this disclosure also includes a urinal or any other apparatus into which a user urinates. A user may be any person or animal. One skilled in the art will recognize that other embodiments may be constructed for testing saliva that include components disclosed herein with respect to urine.

One or more embodiments of the urine analysis system may include a urine collector, such as a cup, a container, a trough, or an absorbent material such as Porex® for example, that may be deployed into or near a toilet bowl so that a user can provide a urine sample into the collector. The urine collector may have a deployed position and a retracted position. In the retracted position, the urine collector may be located within or adjacent to a housing that may be mounted to the toilet. This housing may for example protect the collector from toilet water during flushing and toilet cleaning products when the toilet is being cleaned. In the deployed position, the urine collector may be located inside the toilet bowl, or possibly above the toilet bowl within a cylinder that extends upwards from the top of the interior of the bowl, i.e., so that the collector may be below, at, or above the plane defined by the rim of the toilet. A collector movement mechanism, such as for example a hinge, may allow the collector to move from the retracted position to or from the deployed position. In one or more embodiments the movement of the urine collector from the retracted position to and from the deployed position may be performed by a collector actuator.

One or more embodiments of the urine analysis system may perform urine analysis tests by dispensing a portion of the urine sample in the collector into a reaction chamber. The reaction chamber may contain a single-use or multiple-use test media, for example a reaction zone matrix, which may be used to perform one or more tests. The media or matrix may for example be a sheet of material with one or more test regions, where each test region has specific reagents that perform specific urine conditioning and analysis tests to detect specific substances in the urine. A new test matrix may be provided for each urine analysis session. A bank of unused test matrices may be stored in a test matrix storage chamber. To perform urine tests, a test matrix transport mechanism or reel system may take an unused test matrix from the storage chamber and transport it or advance it to a reaction chamber. A fluid transport system may then dispense urine from the urine collector onto the test regions of the test media matrix. After the test regions have been exposed to urine, a sensor system may then capture one or more reported signals of the exposed test matrix. For example, without limitation, the sensor system may include an optical sensor system that captures one or more images of the matrix or each test region or multiple test regions. One or more embodiments may capture and analyze any type or types of signals, including but not limited to images or optical signals. In one or more embodiments, data may be collected at different time intervals to track reaction of the urine with the test media as a function of time. The signal values may then be transmitted to a processing system that analyzes the data within the system, by the user's handheld device or computer, or by a remote server to determine the results of the tests. For example, without limitation, the data analysis system may include an image analyzer that analyzes images.

After the testing in the test chamber is complete, the test matrix transport system may transport the used test matrix to a waste chamber. A cleaning solution stored in a cleaning solution container may then be flushed through parts of the system to prepare it for subsequent tests. One or more embodiments may contain or use multiple cleaning solutions, for example to support a two-stage cleaning process with a first solution followed by a second solution.

In one or more embodiments the test matrix may have one or more multiple use reaction zones. These multiple use reaction zones may for example contain an array of micro-reactors containing immobilized active reagents that interact with the analytes of interest. Once the reaction or reactions are complete, the micro-reactors may be flushed, and the report signal or signals may be captured with one or more sensors (such as for example an image capture system). The micro-reactors may then be regenerated with an appropriate solution or solutions, which may condition them for the next test.

The urine analysis system may have a wired or wireless communication interface, for example to receive commands or transmit images, numeric data, raw image data, or test results. Data may be encrypted for transmission in one or more embodiments. Transmitted data may be anonymous, or it may have a security key or other identifier for example to match it to the user. Thus, embodiments may meet any medical law requirements, such as HIPAA and for example may be used to facilitate communication of data to a physician or other person. The urine analysis system may have a controller that may for example coordinate the sensors, actuators, processors, and communication interfaces of the system. For example, the controller may perform or coordinate steps such as activating the collector actuator to move the urine collector to its deployed position, activating the test matrix transport system to move a test matrix from the test matrix storage chamber to the test chamber, activating the fluid transport system to transport a urine sample from the urine collector and to dispense a portion of the urine sample onto each test region of the test matrix in the test chamber, activating the image capture system (or other sensor system) to illuminate and capture one or more images (or other signals) of the test matrix in the test chamber, activating the test matrix transport system to move the test matrix from the test chamber to the waste chamber, and activating the fluid transport system to transport cleaning solution from the cleaning solution container to the test chamber.

In one or more embodiments of the urine analysis system, the urine collector may be coupled to an arm that is attached to a hinge on or near the housing, where the housing may for example be mounted to the side of the toilet bowl. Deployment or retraction of the urine collector may be performed by rotating the arm around the hinge, potentially using a collector actuator for example.

In one or more embodiments of the urine analysis system, the test matrices may have a barcode. The barcode may encode or provide an index into various types of information, including for example, without limitation, manufacturing date(s), assembly date, an expiration date, test calibration data, manufacturing specifications, and an identification of the tests incorporated into the test matrix.

In one or more embodiments a user may initiate a urine analysis test by activating a user control, such as for example a "start test" button. This button may be for example a physical button (mounted for example on or near the toilet), or a button on an application or "app" on the user's computer, mobile device or handheld device. When the physical button or button on an app is activated, a command may be sent over the wireless communications interface to the controller of the urine analysis system, indicating that the urine collector should be deployed. Device activation controls may for example include any or all of a physical button on the device, a wireless button on the wall or toilet (like an Amazon Dash™ button, for example) (potentially with multiple buttons for different users), a soft button within a phone app, a handheld device, a biometric sensor like touch id that may for example scan the user's fingerprint, a near field communication tag, a physical gesture such as waving a hand or foot, voice or sound activation, smart sensors on clothing or shoes, controls on any personal device such as a phone, fitness monitor, or smart watch, and automatic urine sample identification.

One or more embodiments of the urine analysis system may include or communicate with an app on a computer, mobile, handheld or any other electronic device that receives test results and displays them to the user.

The image analyzer or other signal analyzer or analyzers of the urine analysis system may be local to the toilet mounted components, or remote from these components. For example, in one or more embodiments, the signal analyzer may be a server that receives image data (or other signal data) over a network connection; the server may then transmit results to the user's mobile device.

In one or more embodiments of the urine analysis system, the sensor system may include multiple LEDs or other light sources, each of which emits a specific wavelength of light or one or more wavelengths or ranges of wavelengths of light. These different wavelengths may be optimal for a particular test or different tests on the test matrix.

Test matrices may contain several test regions; for example, in one or more embodiments test matrices may contain any number of test regions, constrained only by the number of tests that fit in the chamber, and any number of tests per cartridge, for example 6, 20, 30, 60, 180, or more different urine analysis tests or any other number per cartridge. Test regions may include for example both lateral flow tests and colorimetric tests on the same test matrix for example.

In one or more embodiments, the test matrix storage chamber and the waste chamber may have capacity to store at least 180 test matrices. This capacity may for example support daily use of the urine analysis system for approximately 6 months or more.

BRIEF DESCRIPTION OF THE DRAWINGS

The above and other aspects, features and advantages of the invention will be more apparent from the following more particular description thereof, presented in conjunction with the following drawings wherein:

FIGS. 5A, 5B, and 5C show an illustrative urine collector, which for example may be a collector cup in one or more embodiments.

FIGS. 6A, 6B, 6C, and 6D illustrate deploying the urine collection mechanism.

FIG. 6F illustrates an embodiment with a collector that incorporates a trough along a rotating arm. FIG. 6G shows a closeup view of the collector of FIG. 6F, and FIG. 6H shows a cross sectional view of the trough.

FIG. 7B shows an illustrative embodiment with a horizontally oriented test matrix sandwiched between a top clamp through which imaging occurs and a bottom clamp through which urine flows.

FIG. 7E shows an illustrative embodiment with a vertically oriented test matrix and a vertically oriented test chamber.

FIG. 7F shows the embodiment of FIG. 7E with urine partially filling the test chamber.

FIG. 8A shows an illustrative embodiment that employs a reel to reel system for test matrix storage and transport.

FIG. 9 shows spectral response curves for an illustrative colorimetric test that may be performed by one or more embodiments of the invention, illustrating a procedure that may be used to select one or more wavelengths of light to illuminate the test matrix.

FIG. 10 shows several illustrative architectures for analysis of test matrix signals (such as images, for example) to determine urine test results.

FIG. 11 shows an illustrative architecture for an embodiment that incorporates a recommendation engine to provide users with dietary and lifestyle recommendations based on their urine analysis results.

DETAILED DESCRIPTION OF THE INVENTION

A toilet based urine analysis system will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
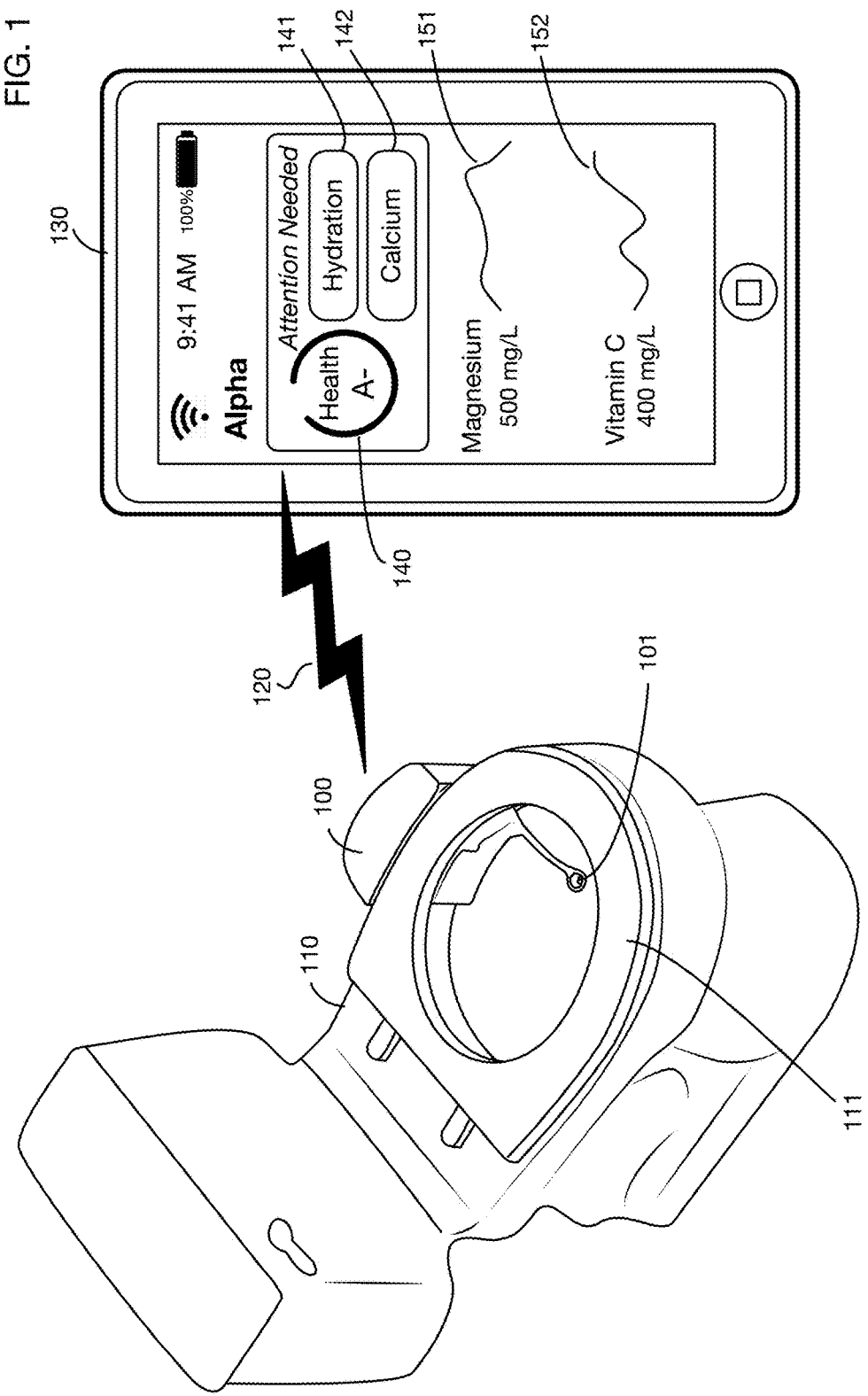
FIG. 1 illustrates an embodiment of a toilet based urine analysis system that collects a urine sample from a user, analyzes various substances in the urine using analytical supplies and equipment attached to the toilet, and transmits results to a remote computer, such as the user's mobile device.

FIG. 1 shows an embodiment of a toilet based urine analysis system 100 attached to toilet 110. In this illustrative embodiment, the system 100 is mounted on the side of toilet 110. In one or more embodiments the urine analysis system may be mounted or attached to any portion or portions of a toilet or may be located in any area or areas proximal to the toilet. In one or more embodiments the urine analysis system or portions thereof may be integrated into the toilet, for example by a toilet manufacturer, installer, or designer. The toilet may be for single user use, family use, company use, senior living facility, clinic, hospital, corporate use, for example corporate compliance, or public use; it may be in any location, including but not limited to a private dwelling, an office building, a commercial building, or a public space. For example, in one or more embodiments of the invention, the device could also be stand alone on a countertop or a cart. Urine may be provided manually from a container, a bedpan, or a urinary drainage bag, which is useful in hospitals and elder care facilities, for patients that have limited mobility, are bed ridden or otherwise are unable to utilize other embodiments of the invention described herein. One or more embodiments may provide a urine analysis system for a pet or domestic animal. The urine analysis system may be integrated or attached for example to a device that the pet or animal may urine into or onto. In one or more embodiments the animal urine analysis system may be standalone, and a person may collect a urine sample from the animal, for example using a container or tool, and then dispense this sample into the standalone urine analysis system. The illustrative urine analysis system 100 has a urine collector 101 that is shown in its deployed position. The deployed position is located in a volume that includes the interior of the bowl of toilet 110. In one or more embodiments the collector's deployed position may be above the rim of toilet 110, for example within a cylinder that extends upwards from a horizontal section of the interior of the bowl at or near the top of the rim. The collector 101 may be of any size and shape. In one or more embodiments the collector 101 may be attached to or integrated into the toilet seat 111. One or more embodiments of the collector may be made from, or coated with, materials that do not allow substances, including but not limited to minerals, proteins, and bacteria, to easily adhere to the collector surface, such as polytetrafluoroethylene (PTFE), liquid-infused polymers, hydrophobic, super-hydrophobic, oleophobic or superomniphobic materials and/or microscopic or nanotechnology materials, for example that exhibit the Lotus effect, or use labyrinths that contain only turbulent flow areas to keep sediment or any other material from settling on a surface.

The embodiment shown in FIG. 1 illustrates a urine analysis system mounted on a toilet. In one or more embodiments the toilet may be a urinal or any other apparatus into which a user urinates. In one or more embodiments the urine analysis system may be attached to or integrated into a urine collection area that may for example be a drain of a shower or bathtub or any other area into which a user may urinate. In one or more embodiments the urine analysis system may be standalone, and may for example be used to receive urine and analyze urine collected by or from a user in any location using any device or container.

In one or more embodiments of the invention, the system may support collection and analysis of other body fluids or materials instead of or in addition to urine. For example, one or more embodiments may also provide a capability to collect and analyze saliva.

Urine is collected in collector 101 and is transported into the analytic components of system 100. These analytic components may perform any desired urine analysis test or tests. In one or more embodiments the system 100 may perform multiple tests, potentially tens or hundreds of tests for example, on a single urine sample collected by collector 101. Tests may involve any type or types of reagents, assays, and detection technologies. Tests may include, for example, without limitation, any one or any combination of lateral flow tests, colorimetric tests, florescence tests, surface plasmon resonance ("SPR") tests, immunoassays (including but not limited to paper-based and liquid immunoassays), homogeneous and immunochromatographic assays, optical sensors, electrical sensors, chemical sensors, label and label-free detection technologies, chromogenic assays, fluorophore-based assays, binding events assays, and electrochemical assays.

Data from tests performed by system 100 may be transmitted to one or more display systems, to databases, to messaging systems, to medical record systems, or to other systems for further analysis. In the illustrative example shown in FIG. 1, data from system 100 is transmitted over a wireless connection 120, such as for example a Wi-Fi or Bluetooth link, to a mobile device 130 used for example by the consumer performing the urine test. Any device or system may receive data from the system 100, over any type or types of links or network connections. For example, in addition to or instead of transmitting data to the user's mobile device 130, the system 100 may send data to the user's physician, to a family member or caregiver, to an insurance company or benefit manager, to a case manager, to a pharmacy, or to a database containing the user's medical record.

In one or more embodiments, data from urine analysis system 100 may also be transmitted to one or more other systems or devices for further analysis. The results of these further analyses may then be sent to the user's mobile device 130 or to any other recipients or systems including those described above. In one or more embodiments the mobile device 130 may perform all or part of the analysis of the data from the urine analysis system.

Test results may be displayed on mobile device 130 or any other system or device in any desired format. In the illustrative example of FIG. 1, an app linked to the urine analysis system displays a summary total health grade 140 (which may for example be a letter grade, a numerical rating, a percentile, or any other measure or measures), and indicators 141 and 142 showing which test results are abnormal or of concern. For other test results, details 151 and 152 show the actual result values and a chart of results over time. One or more embodiments may provide additional information or options such as data or charts on all test results including normal results, explanations of the tests, and suggestions for lifestyle modifications or interventions to improve results.

Figure 2:
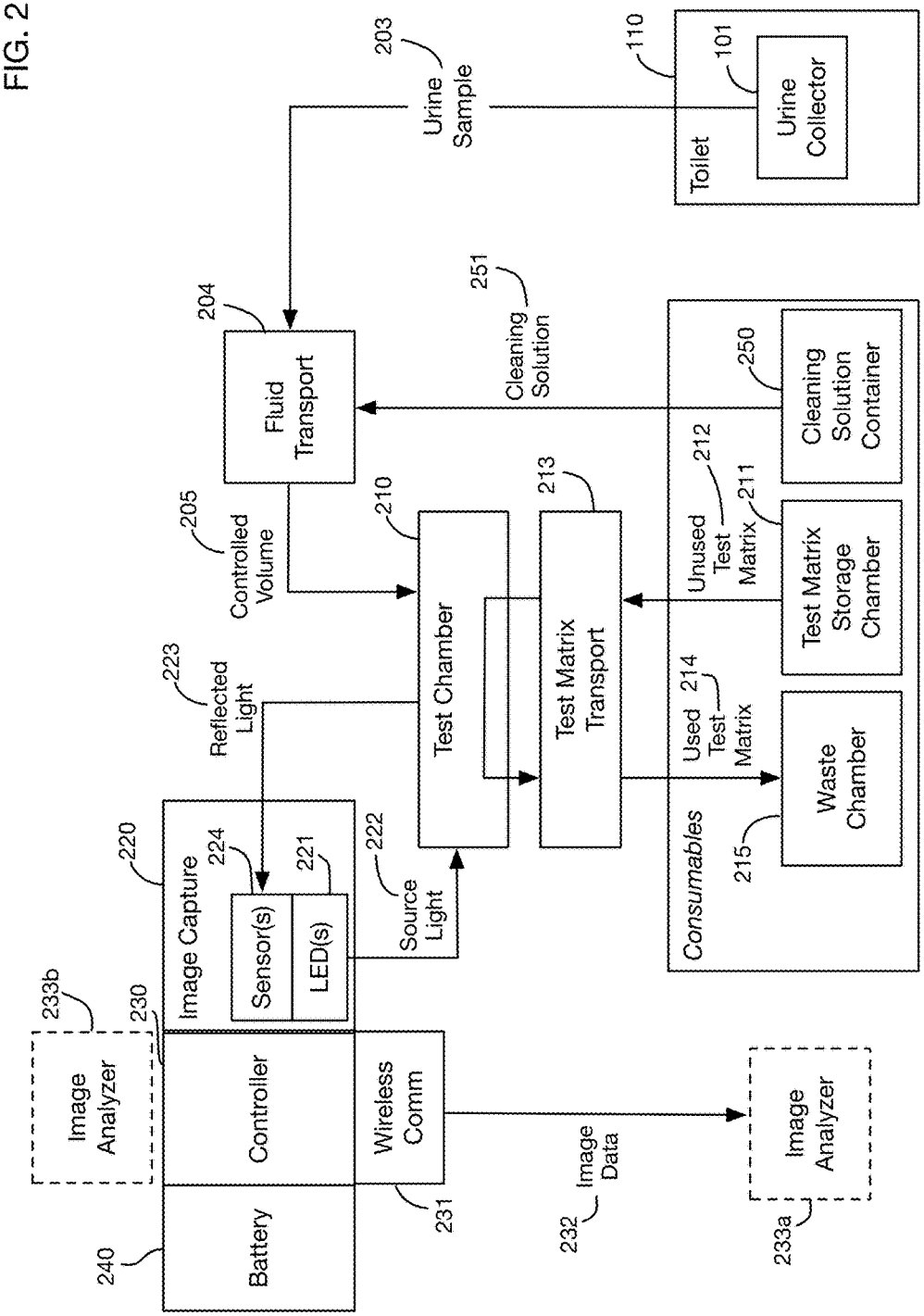
FIG. 2 shows a block diagram of an embodiment of the invention.

FIG. 2 shows a block diagram of an embodiment of the invention. Urine collector 101 is located within or proximal to toilet 110. It collects a urine sample 203. A fluid transport system 204, which may for example comprise pumps, valves, tubes, capillaries, microfluidics systems, or other elements, transports all or a portion of urine sample 203 from the collector 101 to a test chamber 210 for analysis. In one or more embodiments, the collector itself may also act as a test chamber. In the embodiment shown in FIG. 2, tests are performed by dispensing urine onto one or more regions of a test matrix, where each region may have reagents that react with the urine to perform one or more specific tests. The system stores unused test matrices in a test matrix storage chamber 211. A test matrix transport system 213 takes an unused test matrix 212 from the storage chamber 211 and moves it into test chamber 210. The fluid transport system 204 dispenses a controlled volume 205 of urine onto the test regions of the test matrix in the test chamber 210. In the illustrated embodiment, the test matrices are disposable; they are discarded after use. In one or more embodiments, the test matrices may be reusable.

The embodiment shown in FIG. 2 uses optical detection elements, for example photosensor system 220 to measure the reaction of the urine sample with the reagents of the test regions of the test matrix. One or more embodiments may use any type or types of detection technology, including but not limited to optical detection. One or more light sources such as LEDs 221 may illuminate the test matrix with source light 222, which may be of specific wavelength(s) associated with particular tests. Reflected light 223 is measured by optical sensor or sensors 224. Optical sensors 224 may be any desired technology that responds to any type of electromagnetic radiation. For example, without limitation, sensor or sensors 224 may be a photosensor capable of detecting any combination of light reflectance, absorption, or fluorescence, such as for example a CMOS/CCD camera, a photodiode array, or a spectrophotometer. Data from sensors 224 is transmitted to one or more image analyzers to determine the results of the tests. A controller 230 coordinates transmission of the data to the image analyzer. Controller 230 may also coordinate the other sensors and actuators of the urine analysis system, such as for example the fluid transport system 204 and the test matrix transport system 213. In one or more embodiments an image analyzer 233b may be located within or proximal to the urine analysis system. In one or more embodiments an image analyzer 233a may be remote from the urine analysis system, and the controller 230 may use a network interface such as wireless communications interface 231 to transmit image data 232 from sensor 224 to the image analyzer. A battery 240 may provide power to the electrical components of the system; in one or more embodiments power may be supplied from an AC power connection.

After testing is complete, the test matrix transport system 213 may transport the used test matrix 214 from the test chamber 210 to a waste chamber 215. A cleaning process may then be executed to prepare the system for a subsequent test. For example, the system may include one or more cleaning solution containers 250 that contain a cleaning solution. The fluid transport system 204 (or a separate cleaning fluid transport system) may then move a cleaning solution 251 through the fluidics system, the test chamber, or any other portions of the system to prepare for the next test.

In one or more embodiments any or all of the fluid transport system 204, the fluidics system, and the test chamber 210 may be configured with one or more fluid paths that promote turbulent flow of the urine through the system, thereby preventing or reducing buildup of deposits or precipitates in the system that might for example lead to clogging or suboptimal urine flow. Fluid paths may for example incorporate one or more labyrinth shapes to promote this turbulent flow. The system pump may also be controlled in a manner to promote turbulent flow. In one or more embodiments a cleaning solution 251 may be unnecessary when fluid paths provide sufficient turbulence for a self-cleaning system.

Figure 3:
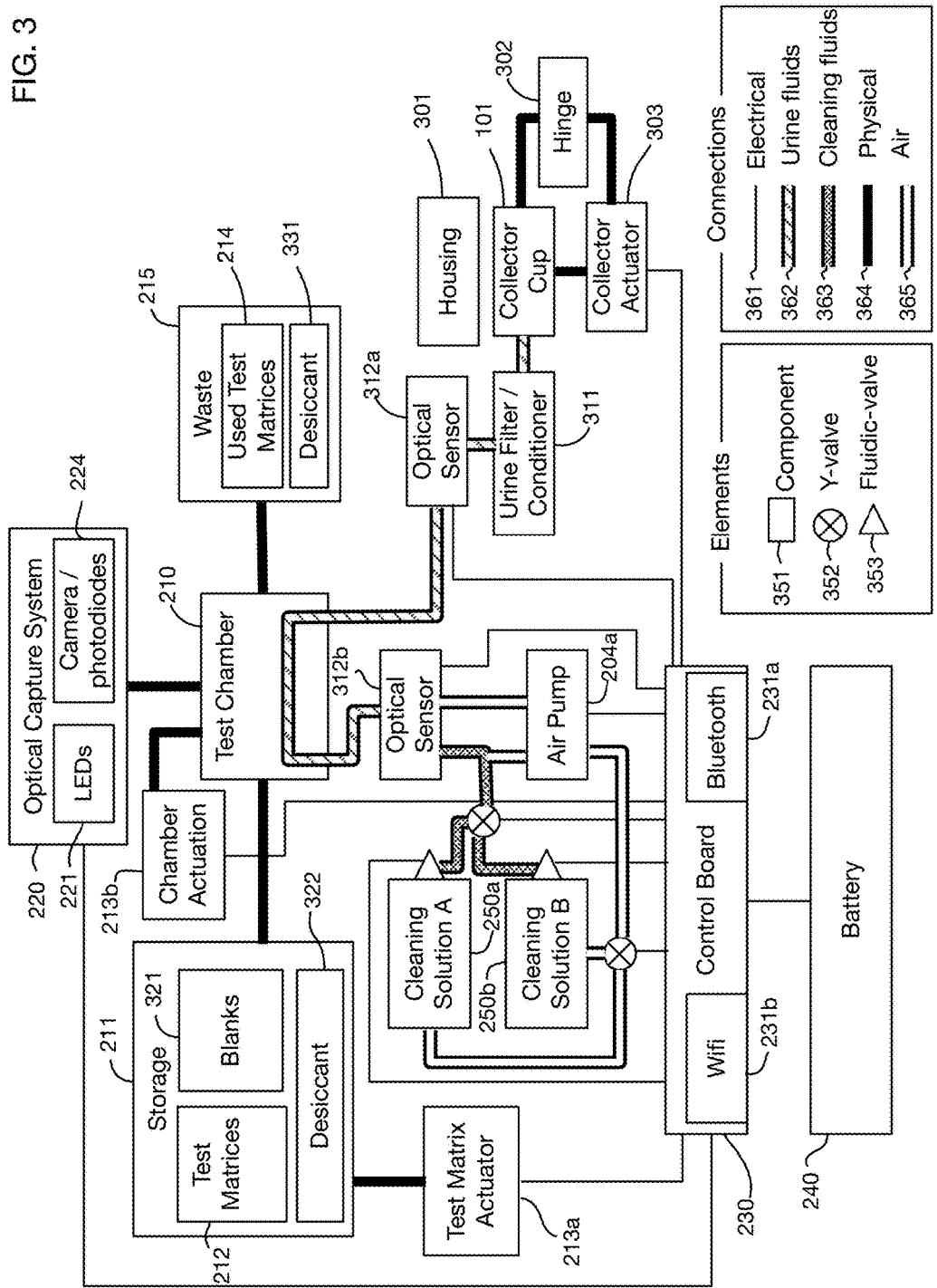
FIG. 3 shows an architectural diagram of an embodiment of the invention that illustrates physical, electrical, and fluid connections.

FIG. 3 shows an architectural diagram of the components and connections of an embodiment of the invention. Elements shown include components 351, Y-valves 352, and fluidic valves 353. Connections illustrated include electrical connections 361, urine fluid connections 362, cleaning fluid connections 363, physical connections 364, and air connections 365.

Collector 101 has a deployed position and a retracted position. In the retracted position, the collector 101 is within or adjacent to a housing 301. The housing 301 may for example protect the collector and other components while the toilet is being cleaned. A hinge 302 allows the collector to move between the deployed and retracted positions. One or more embodiments may incorporate any type or types of mechanisms, including but not limited to a hinge, to allow movement of the collector between the deployed and retracted positions. In one or more embodiments a collector actuator 303 may be actuated to deploy or retract the collector. In one or more embodiments the user may manually deploy or retract the collector. In one or more embodiments, a collector actuator may support a seek mode that causes the collector to move within a pre-programmed pattern and speed to seek for a urine stream until it finds it; this mode may be particularly useful for example for a user standing or seating who does not wish to have to aim the urine stream towards a static collector location or look down to observe where the collector is located. For example, without limitation, in seek mode the collector may sweep across the front half of the toilet bowl (like a windshield wiper) until it detects the urine stream. If the urine stream moves, this may trigger a return to seek mode to find the new location (unless for example sufficient urine has already been collected).

Urine fluid flows from the collector cup 101 to the test chamber 210. A urine filter or conditioner 311 may be in-line in this fluid flow to prepare the urine sample for testing. An optical sensor 312a may detect the flow of urine in this connection line to ensure that the sample is flowing correctly for the test. To perform a test, a test matrix may be moved from a bank of test matrices 212 in storage 211 by a test matrix actuation system 213a; it may be received into test chamber 210 and placed into position by a chamber actuation system 213b. Urine fluid may then be deposited on the test matrix. In one or more embodiments urine fluid may be deposited onto the test matrix incrementally as it moves into or through the test chamber. Alternatively, in one or more embodiments all tests in the test matrix may be exposed to urine simultaneously. After urine has reacted with the test matrix and the correct reaction/incubation time has elapsed, optical capture system 220 may illuminate the test matrix with LEDs 221 or other light sources, and capture images with cameras, photodiodes, or other sensors 224. Sensor data may be sent to control board 230 and transmitted over wireless connections such as for example a Bluetooth connection 231a or a Wi-Fi connection 231b. Electronics and electrical sensors and actuators may be powered from battery 240.

After testing, the used test matrix may be moved to waste storage 215, which contains used test matrices 214. The waste chamber 215 and the unused test matrix storage chamber 211 may include desiccants 331 and 322. One or more cleaning solutions may then be flushed through the system to prepare for additional tests. During cleaning, a blank test matrix may be moved from blanks 321 in storage 211 into the test chamber 210. The embodiment in FIG. 3 shows two cleaning solutions in storage containers 250a and 250b; either or both of these solutions may be used to clean the system. One or more embodiments may use any desired type and number of cleaning solutions. An air pump 204a may be used to transmit fluids such as urine and cleaning solutions. An optical sensor 312b may be used to measure flow of the cleaning solutions or flow of urine out of the system after testing.

Figure 4:
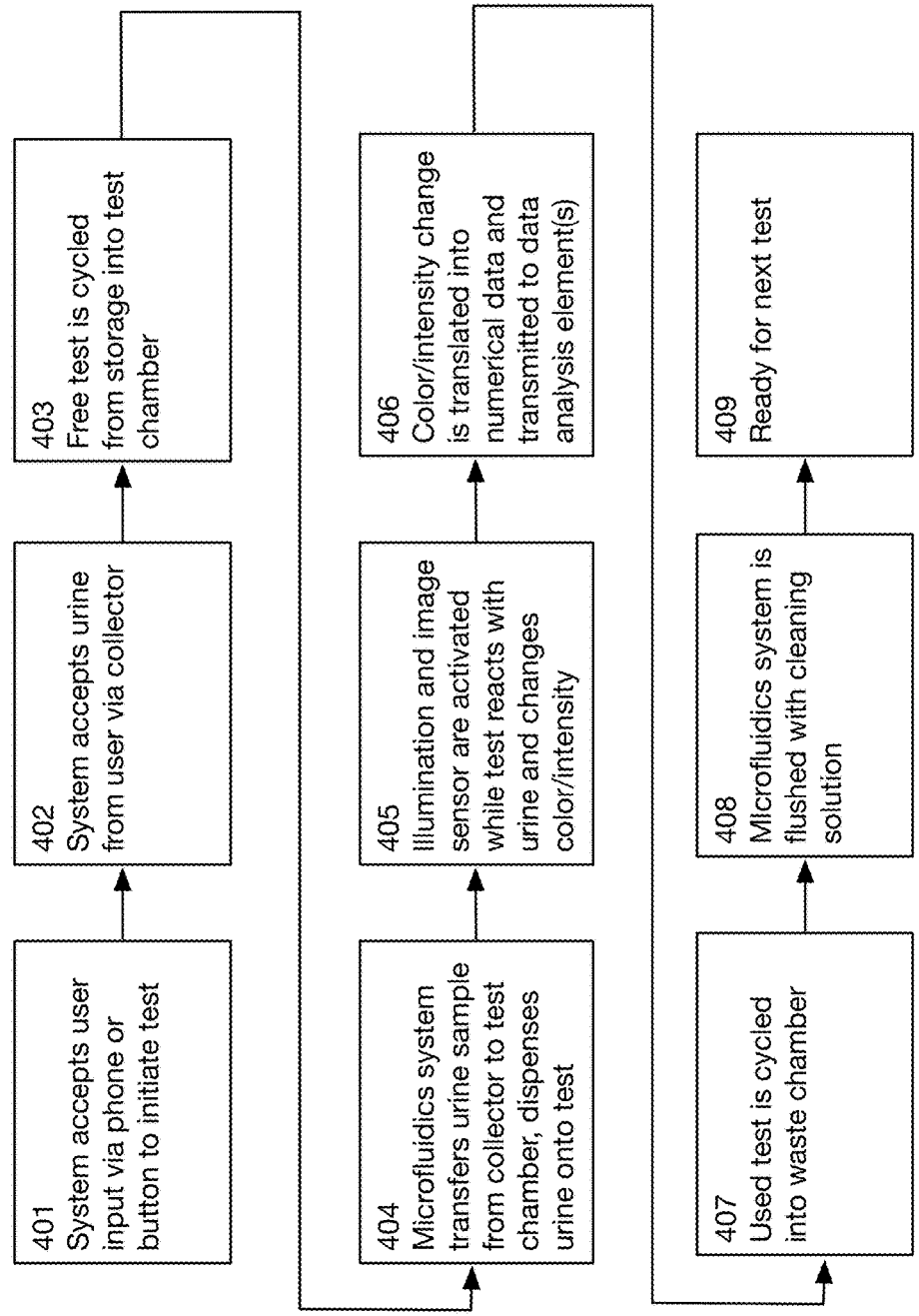
FIG. 4 shows an illustrative flowchart of steps for an embodiment of the invention that collects and analyzes urine.

FIG. 4 shows an illustrative process flow to perform one or more urine tests. Some of these steps may be initiated or coordinated for example by the controller in the urine testing system, by a processor in a user's mobile device, or by a combination thereof. In step 401 the system accepts user input via a computer, such as a mobile device or remote computer or local button for example and initiates a test. In step 402 the system accepts a urine sample from the user, i.e., accepts urine into the collector. In step 403 an unused test matrix is cycled from the test matrix storage chamber into the test chamber. In step 404 a fluid transport system, such as for example a microfluidics system, transports urine from the collector 101 into the test chamber and dispenses urine onto the test matrix regions containing tests. In step 405, the optical system illuminates the test matrix and captures images with one or more sensors to detect changes in color or intensity from the reaction of urine with the reagents on the test matrix. In step 406, the data captured by the imaging sensor or sensors on color or intensity is transmitted to one or more image analysis elements. Image analysis elements may be integrated into the urine testing system or remote from the system. In step 407, the used test matrix is moved to the waste chamber. Then in step 408, the fluid transport system is flushed with cleaning solution. After cleaning, in step 409 the system is ready for a subsequent test.

FIGS. 5A, 5B, and 5C show several views of an illustrative urine collector that may be used in one or more embodiments. FIG. 5A shows collector 101 in the deployed position, located within or above the toilet bowl. FIG. 5B shows a close-up view of cup 101. Urine flows along tube 501 from the collector to the urine analysis components. An exit hole 502 provides a drain for excess urine in the cup. FIG. 5C shows a side section view of cup 101. Urine flows through a narrow circuitous path from the cup into tube 501; this path may function for example as a urine filter.

FIGS. 6A through 6D shows illustrative mechanisms that support deployment of the urine collector from the retracted position. A user may initiate deployment by pressing a physical button 601, which may for example be installed on a wall in a bathroom or on the toilet itself. The button may have a wireless communications interface that transmits a signal to the wireless interface 231 of the urine analysis system mounted to toilet 110. In one or more embodiments the button 601 may be coupled to the urine analysis system by a wired connection. Alternatively, a user may use an app on a mobile device 130 and may for example initiate deployment by pressing a control 602 on the app that sends a wireless signal to the urine analysis system. One or more embodiments may support mechanisms to initiate deployment of the collector 101 without an explicit command from the user; for example, the system may use image capture devices or other sensors to recognize when a user is proximal to toilet 110 and may deploy automatically when a user is present.

FIG. 6B shows an embodiment of the system with urine collector 101 in the retracted position, in this embodiment underneath housing 301. When the start deployment command is received, an actuator rotates the arm holding collector 101 around a hinge, deploying the collector cup. FIG. 6C shows the collector cup partially deployed, and FIG. 6D shows the collector cup fully deployed and ready to collect a urine sample.

Figure 6E:
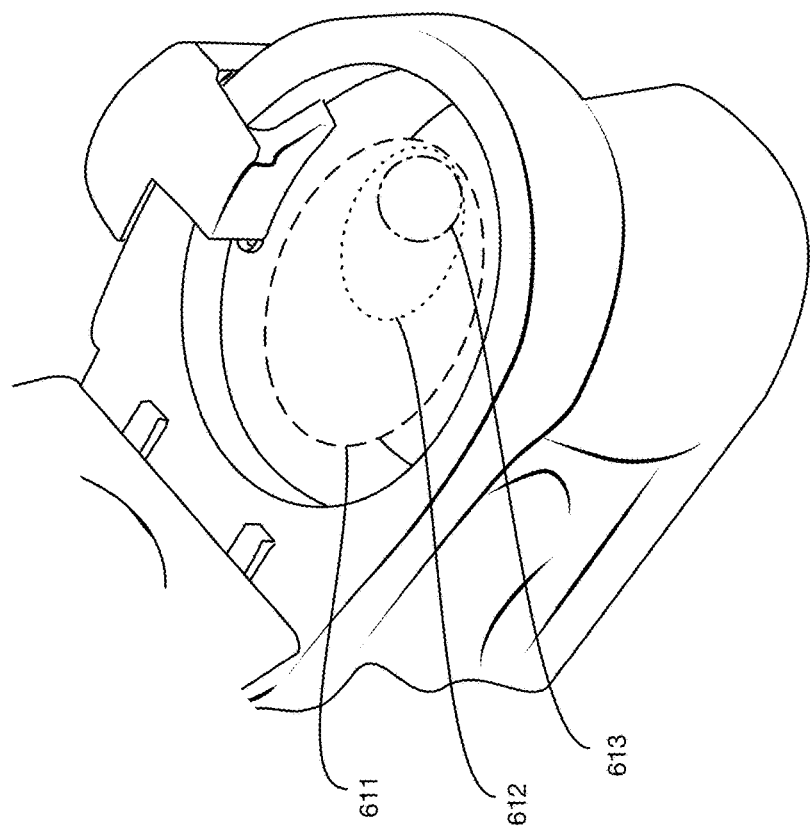
FIG. 6E illustrates a challenge in collecting urine that may be dispensed by the user anywhere within a wide area within the toilet.

A desirable feature of a toilet-based urine analysis system is to be able to collect urine when the user uses the toilet, without requiring the user to aim at a collector cup. FIG. 6E illustrates a challenge in accomplishing this objective: users may dispense urine at a wide variety of locations within the toilet. For illustration, zone 611 is an area into which a male user standing may typically dispense a urine stream. Zone 612 is an area into which a female user seated may typically dispense a urine stream. Zone 613 is an area into which a male user seated may typically dispense a urine stream. Since zone 611 contains the other two smaller zones 612 and 613, a collector that works to collect urine from a stream anywhere in zone 611 will work for all three cases. Collecting urine from anywhere within zone 611 may be accomplished in one or more embodiments for example with a collector made of a mesh or fabric material that unfolds to cover the full area. The collector may for example be anchored at two or more points on the toilet and may deploy to cover the entire zone 611. The collector may for example be constructed of a hydrophobic anti-stick fabric, or a wire mesh. When collection is completed, in one or more embodiments the unfolded collector may for example be sucked back into a tube, or folded up like a fan, to get rid of excess liquid.

One or more embodiments may alternatively or in addition provide a collector capable of sweeping across the entire zone 611, detecting when it is under the urine stream, and remaining positioned in the stream long enough to collect an adequate volume of urine. Detection of urine flowing into the collector may for example use one or more pressure sensors, force sensors, liquid sensors, flow sensors, capacitors, or any other mechanism to detect the urine flow. Illustrative embodiments employing a sweeping collector may include for example an embodiment with collector cup at the end of a jointed collector arm, with actuators to rotate the arm and to rotate at the elbow to sweep the collector cup across the entire collection zone using two degrees of freedom. Another illustrative embodiment may for example use a collector incorporated into a rotating arm without an elbow joint, having a single degree of freedom, with the collector formed as a trough along the arm. An illustrative trough collector may for example have a C-shaped cross section with a slot facing upward, similar to a straw with a split cut into it. A potential advantage of a trough collector is that only a single actuator may be needed to sweep the collector across the collection zone.

FIG. 6F shows an illustrative embodiment with a trough collector 621, which rotates around a joint 622 to sweep across the collection zone. FIG. 6G shows a closeup view of the collector arm 621. FIG. 6H shows a cross section of the arm 621, illustrating a roughly circular trough 623 with a section removed for collection, and lips or flanges 624 that extend from the circular area outward to the sides to capture urine across a wider zone and direct it into the trough. Urine may for example vortex around the trough instead of splashing out, and then flow inward along the arm to the analysis system. The geometry of this illustrative trough collector minimizes splashing due to its minimal splash surface. One or more embodiments may have a trough collector that does not include lips or flanges, for example with a trough geometry that has a large trough surface to facilitate collection but has a shape or material that reduces splashing off of this surface.

Figure 7:
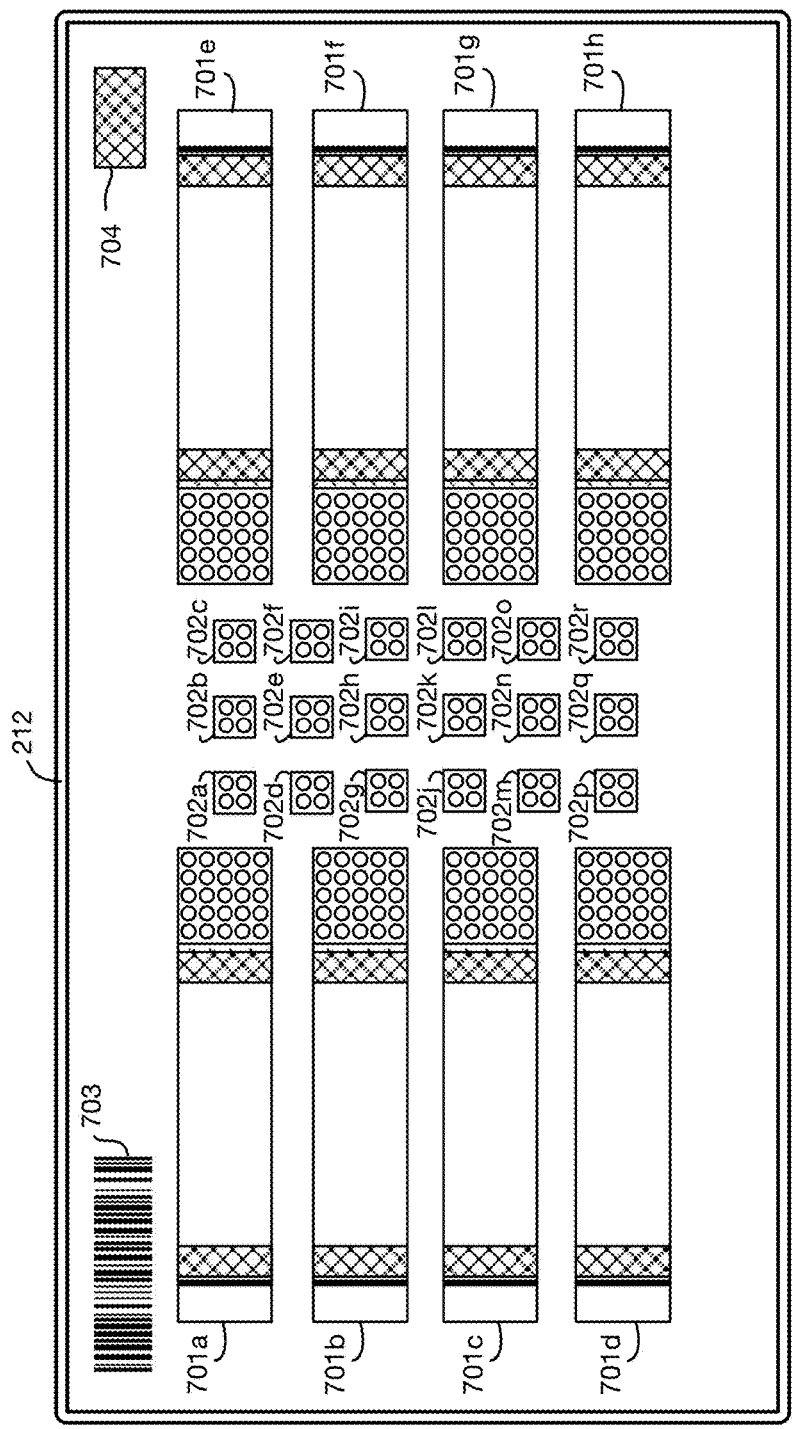
FIG. 7 shows an illustrative test matrix with various reagents embedded in different regions to perform different urine analysis tests.

FIG. 7 shows an illustrative test matrix 212. Test matrices may contain any number and any type or types of urine tests. For example, the test matrix may be divided into regions, each of which is impregnated with reagents and materials that condition the sample and perform one or more specific test reactions. The illustrative test matrix 212 contains 8 lateral flow immunochromatography strips in regions 701a through 701h, and 18 colorimetric test pads in regions 702a through 702r. Lateral flow strips 701a through 701h may each perform multiple tests; for example, in one or more embodiments each strip may perform 2 to 4 tests per strip. An illustrative size of a test matrix may be for example 38 mm high by 72 mm wide, by 0.9 mm deep. An illustrative size for a lateral flow strip may be for example 5 mm high by 20 mm wide. An illustrative size for a colorimetric test pad may be for example 2 mm wide by 2 mm high. These sizes are illustrative; one or more embodiments may use larger test matrices or smaller test regions to achieve a higher density of tests per test matrix. For example, a test matrix 76 mm high by 72 mm wide may contain at least 16 lateral flow strips and 36 colorimetric test pads, using the same test region dimensions as those described above; with two tests per lateral flow strip, this test matrix may contain over 60 different tests. A test matrix may have multiple layers, including for example a backing, one or more layers for reagents, and a top laminate layer. Materials may be selected to absorb sufficient urine sample volume to perform the tests, and to release the volume to the regions with reagents to perform the desired assays. The top laminate layer may have perforations through which urine flows when dispensed by the fluid transport system. Different volumes may be required for lateral flow tests and colorimetric tests. Urine may be deposited along the test matrix as it moves into and through the test chamber; as a result, different regions may be exposed to urine for different period of time. Therefore, perforation sizes may be different for different tests on the test matrix to compensate for this variation in exposure times and for different urine volumes needed for different tests.

Illustrative amounts of urine required for tests in one or more embodiments of the test matrix may be for example approximately 50 microliters for each colorimetric test and approximately 150 microliters for each lateral flow test. The total amount of urine sample required for a test matrix with dozens of tests may be therefore on the order of 2 milliliters. (For example, for 18 colorimetric tests and 8 lateral flow tests, the urine amount required may be approximately 50×18+150×8=2100 microliter=2.1 milliliter.) This illustrates that one or more embodiments of the system may not need to collect a large amount of urine from the user to perform all of the tests in the test matrix.

The test matrix may also contain one or more barcodes, such as barcode 703, or similar identifying marks or elements. Barcode 703 may directly or indirectly indicate information about the test matrix, such as its manufacture date, its expiration date, calibration information, or identification of the tests incorporated into the test matrix. This information may be integrated into the barcode or may be accessible in a database indexed by the barcode. In one or more embodiments, the barcode information (or information indexed by the barcode) may also be used by the controller of the urine analysis system to control various test parameters, such as the amount of urine dispensed onto the matrix, the amount of time of exposure to urine for the test, and the wavelengths of light used to illuminate the test matrix. Test matrix 212 may also contain one or more other regions for calibration or quality control, such as for example humidity test validation marker 704. These calibration or quality control regions may be imaged and analyzed to ensure that the tests are valid or to compensate for example for environmental factors or test matrix degradation.

Figure 7A:
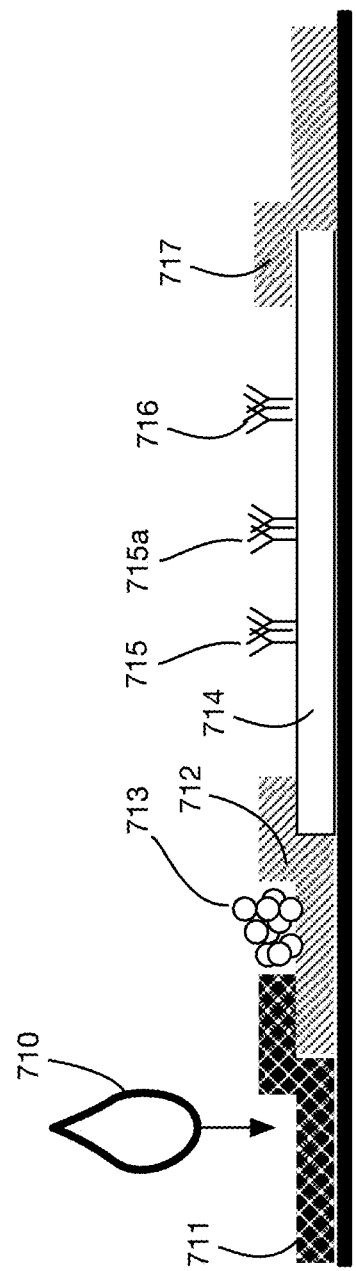
FIG. 7A shows an illustrative embodiment of a lateral flow test.

FIG. 7A shows an illustrative embodiment of a lateral flow assay that may be incorporated for example into test matrix 212. Liquid sample and buffer 710 are dispensed onto a sample pad 711. An absorbent pad 717 on the opposite side of the lateral flow assay provides a pulling force that moves liquid through the stages of the test. First the sample liquid flows to conjugate pad 712, into which a detection conjugate 713 is embedded. The sample and conjugate then flow into nitrocellulose membrane 714. As the lateral flow along membrane 714 continues, the sample and conjugate reach the test line 715, which contains material that reacts with the analyte being tested for. If enough analyte is present, the test line may for example change color and the color change or intensity of the color may indicate whether the analyte is present and in what quantities. A benefit of one or more embodiments of the system is that test results may be quantitative, rather than simply binary (analyte present or not present); using the systems optical imaging for example combined with analysis software, the intensity of the color or other features of the test line may be analyzed to determine the amount of analyte present. One or more embodiments may incorporate lateral flow assays with multiple test lines that may for example test for multiple analytes on the same assay; the assay shown in FIG. 7A has a first test line 715 and a second test line 715a. After reaching the test line or test lines, flow continues to control line 716, which indicates that the sample and conjugate solution has reached this area, thereby showing that the test is valid.

In one or more embodiments, test matrices may incorporate one or more tests that require a multistep chemical reaction. These tests may be performed for example using multiplexed lateral flow strip or vertical flow stacks. A multiplexed lateral flow strip may for example have multiple test lines per strip. In vertical flow stacks, sample and conjugate flow vertically and may be guided into multiple channels in parallel and into multiple test areas in series. Illustrative tests that may require multi-step assays include for example vitamins B7, B9, and B12, and other targets that cannot be measured with single step colorimetric tests.

In one or more embodiments, test matrices may be configured with perforations on the "exposure side" of the matrix through which urine is delivered, with optical imaging performed on the opposite "read side" of the matrix. For example, one or more embodiments may perform tests by clamping and sealing the test chamber against the exposure side (the side with holes) and filling the chamber with urine. Urine may for example flow through the holes at a controlled rate (based for example on hole size and pattern) and saturate the absorbent material. The sensor or sensors may look at the read side and record signals as each assay changes color/intensity over time after urine exposure; this approach may increase the reliability of the test results for example compared to taking a single reading after a countdown time. One or more embodiments may expose the tests to urine and take multiple readings at known time intervals as the test color/intensity changes. Since different tests may require different amounts of sample, flow rates may be controlled individually for each test in the test matrix by altering the hole pattern opposite that test.

In one or more embodiments the test chamber may be configured for example with the optical system on top of the chamber, with urine entering from the bottom of the chamber, and with the test matrix oriented horizontally between the urine flow and the optical system. FIG. 7B illustrates an embodiment with a test chamber configured in this manner. The long axis of the test chamber in this embodiment is horizontal. A top clamp 721 and a bottom clamp 722 are clamped against test matrix 212, using for example a moveable top clamp driven by an actuator. O-rings 729a on the top clamp and 729b on the bottom clamp may provide a seal. The read side 723 of the test matrix is facing upward and the exposure side 724 of the test matrix is facing downward. Upper clamp 721 has a transparent base 726, made for example out of glass or plastic, through which image capture system 220 can obtain optical signals from the test matrix 212. The read side 723 of the test matrix may for example be covered with a transparent laminate backing 727. Imaging may occur through this laminate backing structure and through the transparent base 726. Urine may enter vertically through a path 725 from the bottom to perform a test. Urine may fill the test chamber 728 and flow through perforations on the exposure side 724 to reach the tests embedded in read side 723. In one or more embodiments the flow of urine into test chamber 725 may be facilitated by vacuum suction to pull urine into the chamber. In one or more embodiments a pump may push urine into test chamber 725 without requiring vacuum suction. After a test is performed, urine may exit test chamber 728 through the same path 725 or through a different path. The vertical orientation of the urine flow path may for example facilitate draining of the test chamber after testing. Another potential benefit of this orientation is that as the urine flows into test chamber 728, all perforations on exposure side 724 are exposed to urine simultaneously.

One or more embodiments may orient the components of FIG. 7B (or similar components) horizontally, rather than vertically as depicted in FIG. 7B, and may orient the long axis of the test chamber vertically, rather than horizontally as depicted in FIG. 7B. FIG. 7E shows an illustrative embodiment with a horizontally oriented stack. In this embodiment the long axis of test chamber 728 is vertical, rather than horizontal as shown in FIG. 7B. Urine entry and exit path 725a is at the bottom of the test chamber 728. This embodiment also illustrates a vacuum line 725b at the top of test chamber 728, which may provide suction to assist in filling the test chamber. A potential benefit of this orientation is that urine fills the test chamber from bottom to top; therefore, the perforations on exposure side 724 are exposed to urine for different periods of time as the water line of the urine in the test chamber rises over time during filling. This difference in exposure times may be useful in some situations where different tests in test matrix 212 require different amounts of time. FIG. 7F illustrates the embodiment of FIG. 7E with a partially filled test chamber 728. Urine has reached and flowed through perforation 724a in exposure side 724; hence the test or tests fed by this perforation may have started reacting, while the other tests have not yet started. In one or more embodiments the rate of filling of test chamber 728 may be precisely controlled to provide precise urine exposure times for each test. In one or more embodiments, controlled filling of the test chamber may be further combined with differences in the perforation sizes or patterns behind each test to further control the exposure time and rate of urine flow for each test.

Figure 7C:
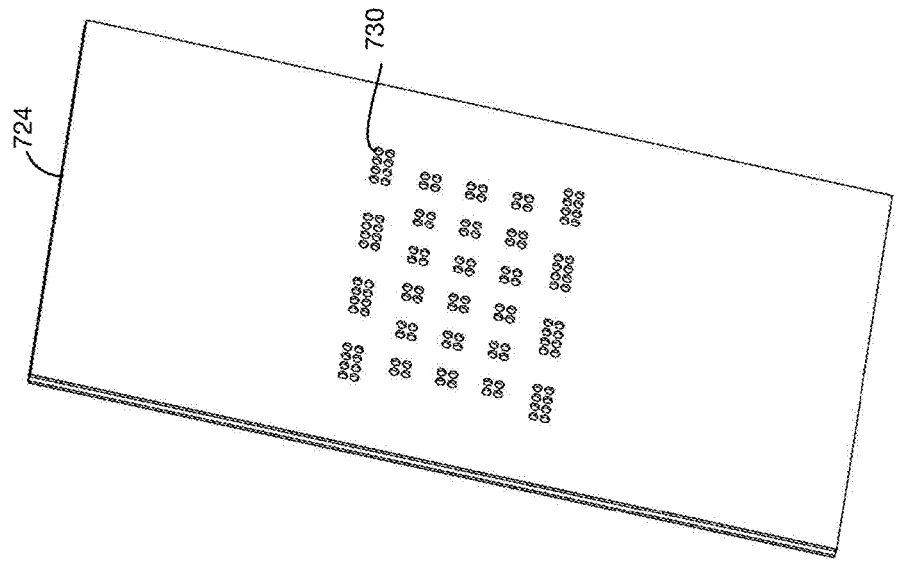
FIGS. 7C and 7D show the read side and exposure side, respectively, of an illustrative test matrix that may for example be used in conjunction with the test chamber of FIG. 7B.
Figure 7D:
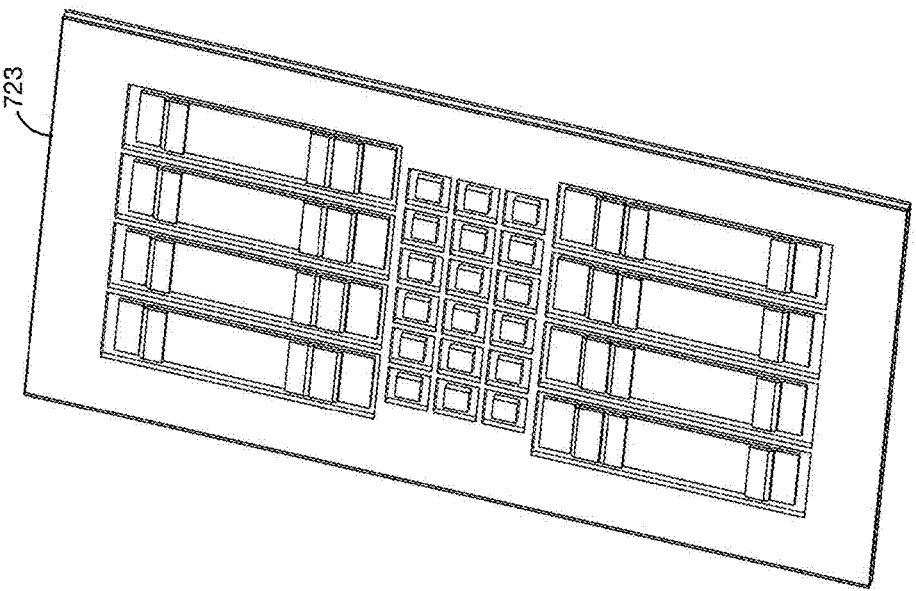

FIGS. 7C and 7D show the read side 723 and exposure side 724, respectively, of an illustrative test matrix that may for example be used with the test chamber of FIG. 7B in one or more embodiments. In this illustrative test matrix, the individual lateral flow and colorimetric tests are separated by dividers to prevent cross contamination. The exposure side 724 has holes or other perforations such as hole 730 through which urine flows to reach the test pads.

In one or more embodiments, rather than exposing all test pads to urine directly via the exposure side of a test matrix, a test matrix may for example have a single sample pad (or a limited number of sample pads), and the matrix may include fluid paths such as glass fibers through which urine is wicked to all of the tests, pulled for example by absorbent pads via capillary action. In general, the test matrix may have any number and configuration of fluidics paths integrated into the matrix to enable delivery of urine to tests. One or more embodiments may incorporate a lateral flow test that has one or more colorimetric tests located in the middle of the lateral flow strip, so that the lateral flow action itself delivers urine to multiple tests. In one or more embodiments, multiple fluidics paths may be integrated into the test chamber to enable separate delivery of urine to different tests or groups of tests, or to more precisely control the timing of urine delivery to each test.

Figure 8:
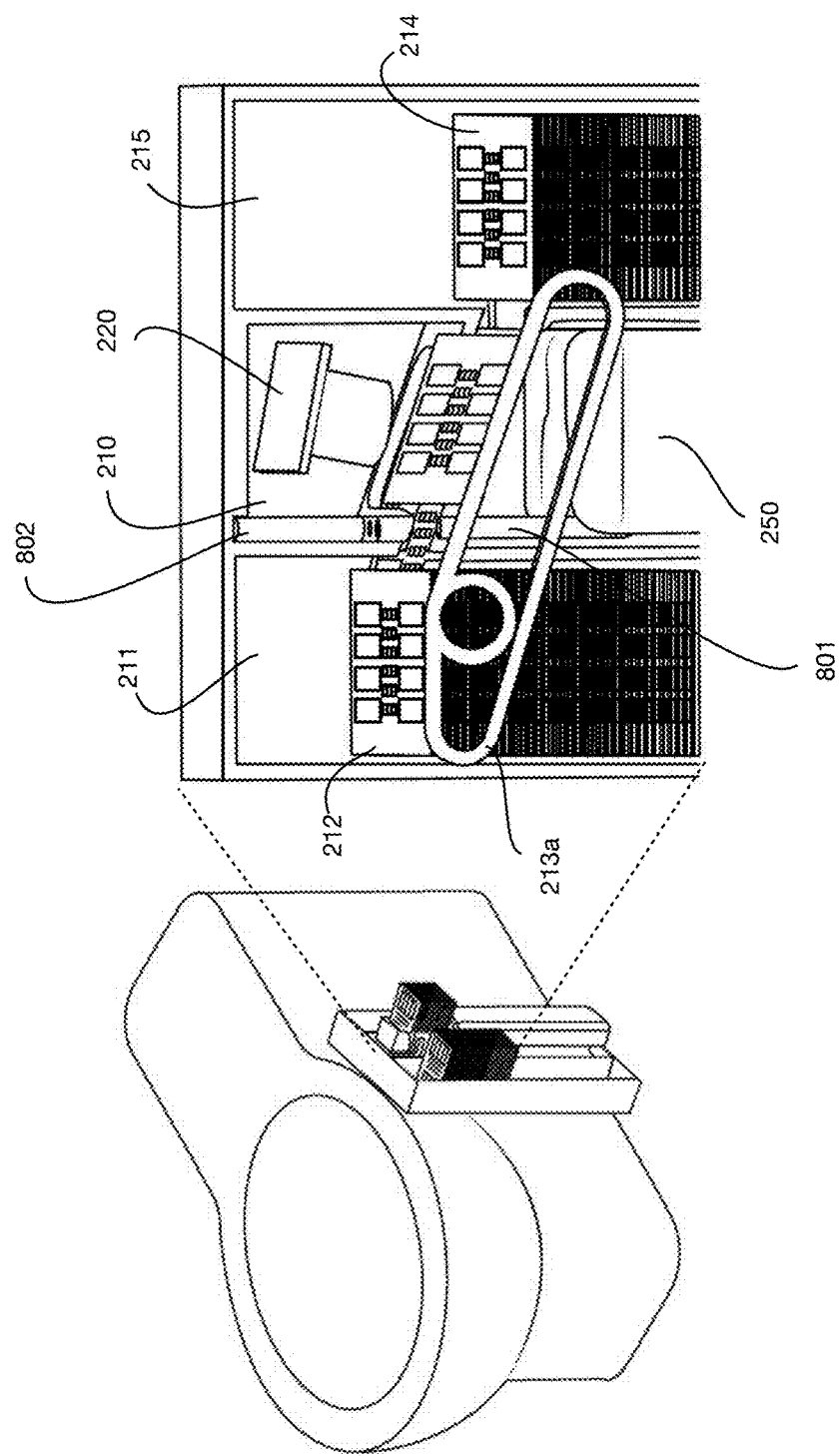
FIG. 8 shows illustrative compartments and mechanisms for storage, use, and disposal of test matrices.

FIG. 8 shows the internal structure of the test matrix storage chamber 211, the test chamber 210, and the waste chamber 215 for one or more embodiments of the invention. In this illustrative embodiment, the test matrices are stored in a stack, and test matrices are moved from the top of the storage stack 212 to the test chamber 210, and then to the top of the waste stack 214 in the waste chamber 215. The unused test matrix stack and the waste stack may for example be contained in removable magazines that are inserted into the test matrix storage chamber 211 and waste chamber 215 respectively.

FIG. 8 illustrates test matrix actuator 213*a*, which may for example be a conveyor system that takes the top unused test matrix 212 from the storage stack, moves it to test chamber 210 for testing, and then moves the used test matrix to the top of waste stack 214. Cleaning solution container 250 is located between the unused test matrix stack and the used test matrix stack; tube 801 carries cleaning solution from the cleaning solution container 250 into the test chamber. Tube 802 carries urine into the test chamber to be deposited onto the test matrix. Optical capture system 220 illuminates and images the test matrix.

One or more embodiments may alternatively store test matrices in a circular cartridge, and may for example spool a reel of test matrices between a storage cartridge and a waste cartridge. FIG. 8A shows an illustrative embodiment of a system that employs a reel to reel system for test matrix storage and transport. For example, unused test matrices may be stored in reel 811 and spooled through test chamber 210 for testing, then wound around reel 812 for disposal. An actuator for example may rotate reel 812 to pull new test matrices into the chamber for testing, and out of the chamber for disposal. A tensioning system may be used to keep the spool in position when it is not actuated and to ensure that the matrices spool smoothly from the storage cartridge through the test chamber to the waste cartridge. FIG. 8A also shows an illustrative cleaning solution container 250 and battery 240. An illustrative reel may for example store 30 tests per cartridge, with two blanks between each test; an illustrative size for the reel to reel mechanism in this configuration may be for example approximately 85 mm deep by 162 mm wide. Another illustrative reel may for example store 180 tests per cartridge, with two blanks between each test; an illustrative size for the reel to reel mechanism in this configuration may be for example approximately 85 mm deep by 240 mm wide. The 30 tests per cartridge system may have for example have two 135 mL containers for cleaning solution, using three washes per test. The 180 tests per cartridge system may for example have a single 950 mL container for cleaning solution, using two washes per test. The configuration may be rotated 90 degrees in either direction so that battery 240 is on the top or bottom in other embodiments of the invention.

One or more embodiments may illuminate the test matrix with selected wavelengths of light to maximize the sensitivity of one or more urine analysis tests. Different tests may respond to different wavelengths; therefore, one or more embodiments may provide several different wavelengths for illumination of the test matrix. FIG. 9 illustrates an example of selecting an optimal wavelength for a specific test. The chart shows the response of reflectance 903 to different concentrations of potassium 901 as a function of the wavelength 902 of illuminating light. Curve 904 shows the best sensitivity, corresponding to a wavelength of 565 nm. Other assays may respond better to different wavelengths; hence in one or more embodiments the optical capture system may provide various wavelengths for illumination. In one or more embodiments these different wavelengths may be provided for example by different LEDs, each emitting one of the desired wavelengths. In one or more embodiments a diffraction grating may split a single source of incident light into various wavelengths that may be used for test matrix illumination. A diffraction grating may also be used to divide reflected light into different wavelength components like a prism. Diffracting different wavelengths at different angles onto different regions of an optical sensor (such as for example a CMOS sensor) creates a type of spectrophotometer.

Images of the test matrix may be analyzed to determine the results of the urine tests embedded in the test matrix. An image or other signals to be analyzed may be any data captured by any sensor or sensors of the urine analysis system. Analysis of images or other signals may be performed local to the urine analysis system, remote from the system, or via a combination of local and remote analysis. FIG. 10 shows several illustrative alternatives for the organization of data analysis. One or more images 1001*a* or other signal data are obtained by sensors 224. In one or more embodiments this data may be transmitted to a local data analysis processor or processors 233*b* integrated into the urine analysis system mounted to the toilet. Results 1002*a* may be transmitted for example over wireless channel 120 to mobile device 130 or other systems for storage, display, or further analysis. A second alternative is to analyze signal data on the mobile device 130: signals 1001*b* may be transmitted over wireless channel 120 to mobile device 130 and analyzed on processor 233*a* in the mobile device, and results 1002*b* may be displayed on the mobile device or otherwise stored or transmitted elsewhere. A third alternative is to analyze signal data on a server or other systems remote from both the urine analysis system and the user's mobile device: for example, signals 1001*b* may be sent to mobile device 130 and signals 1001*c* may then be forwarded (for example over an Internet link) to server 233*c* over network or Internet 1010; results 1002*c* may be sent back to mobile device 130 for display or otherwise stored or transmitted elsewhere. In one or more embodiments, server 233*c* may be multiple servers or a network of any systems that may jointly analyze the signal data 1001*c*. Combinations of these approaches may be used in one or more embodiments, with some aspects of signal analysis occurring locally and others remotely.

One or more embodiments may include or utilize a recommendation engine, which may for example incorporate algorithms that convert multi-point health data sets into dietary and lifestyle recommendations. Recommendations may be based on combined measurements of multiple factors over time. This approach provides several potential benefits since the body's absorption and use of specific vitamins or minerals may depend on the presence of other vitamins or minerals. An example is vitamin B9 which can't be effectively utilized without adequate levels of Vitamin B12 (as well as Vitamin B6 and Iron). Magnesium utilization depends on levels of Vitamin B6, Calcium, Potassium, Zinc, etc. Zinc utilization depends on levels of Copper. Copper utilization depends on levels of Vitamin C, Iron, and Zinc. Vitamin C utilization depends on levels of Iron. Since embodiments of the system may measure many of the body's important vitamins and minerals (along with hydration, amino acids, hormone levels, and other health metrics) on a daily basis, a new layer of data may be created as users implement dietary recommendations and see the results in real time. Providing continuously updated recommendations and daily monitoring of results offers significantly more potential than the current approach in the art of obtaining yearly test results at an annual checkup and rechecking results months later after recommended changes have been implemented. Results may be personalized to each unique individual based on sex, height, weight, and other factors. Actionable recommendations may be rapidly tested and validated or adjusted by a machine learning or artificial intelligence process coupled to the recommendation engine. The recommendation engine may be programmed with medical and nutritional input from health advisors and a machine learning system may be incorporated to update the recommendation engine as more data is collected. Recommendations may be displayed as results 1002b on electronic device 130 for example, or on any other computer, such as a physician's computer, such as server 233c or any other computer connected to Internet 1010, for example in conjunction with appropriate levels of security for sensitive health information.

FIG. 11 shows an illustrative architecture for an embodiment that includes a recommendation engine. Urine analysis system 100 collects data over time, which may be stored for example in a user history 1101. This history tracks multiple results over time. Based on the user's results and trends, a recommendation engine 1102 analyzes the data and transmits recommendations to a user device such as mobile device 130. Transmitted recommendations may for example also include links or other mechanisms to allow users to purchase or order vitamins, drugs, nutraceuticals, food, supplements, or other products. Recommendations may also be based on a user profile 1107, which may for example include the user's gender, age, weight, medical conditions, or other relevant information. The recommendation engine 1102 may for example access a knowledge base 1103 to develop the recommendations for the user. Knowledge base 1103 may incorporate data from medical and nutritional advisors 1104, such as scientifically supported algorithms that determine effective recommendations or interventions. In one or more embodiments knowledge base 1103 may also be constructed or updated based on a machine learning system 1105, such as a deep learning network or any other learning system. A machine learning system 1105 may for example analyze data 1106 that includes measurements, recommendations, and outcomes across multiple users, and may update knowledge base 1103 by learning which recommendations and interventions may improve outcomes.

While the invention herein disclosed has been described by means of specific embodiments and applications thereof, numerous modifications and variations could be made thereto by those skilled in the art without departing from the scope of the invention set forth in the claims.

What is claimed is:

1. A toilet based urine analysis system comprising:
a urine collector configured to collect urine from a user, wherein
said urine collector comprises a deployed position and a retracted position;
wherein when said urine collector is in said deployed position said urine collector is configured to collect urine and is outside of a housing, wherein said housing is integrated with said toilet, and wherein said retracted position is within or adjacent to said housing;
wherein in said deployed position, said urine collector is inside a volume comprising an interior of a bowl of said toilet and below a rim of said toilet; and
wherein in said retracted position, said urine collector is within or adjacent to said housing that is integrated with said toilet; and,
a collector movement mechanism configured to allow movement of said urine collector from said retracted position to said deployed position, and from said deployed position back to said retracted position;
a collector actuator configured to actuate said movement of said urine collector from said retracted position to said deployed position, and from said deployed position back to said retracted position,
one or more of an optical sensor, a pressure sensor, a force sensor, a liquid sensor, a flow sensor and a capacitor that detect whether said urine is flowing into said urine collector when said urine collector is under said urine stream and positioned to collect a volume of said urine;
a controller coupled to said collector actuator and to said one or more of an optical sensor, a pressure sensor, a force sensor, a liquid sensor, a flow sensor and a capacitor,
wherein said controller is configured to coordinate said collector actuator and said one or more of an optical sensor, a pressure sensor, a force sensor, a liquid sensor, a flow sensor and a capacitor,
wherein said urine collector is configured to seek a urine stream using a seek mode until said urine collector detects said urine stream, such that said urine collector is further configured to sweep across an area to collect said urine from said urine stream during said seek;
wherein said collector actuator supports said seek mode that causes the urine collector to move within a pre-programmed pattern and speed to seek said urine stream until said urine collector detects said urine stream, and
wherein when said urine stream moves, said collector actuator triggers a return to seek mode to detect a new location of said urine stream;
a test chamber configured to contain a test matrix comprising a plurality of test regions,
wherein each test region of said plurality of test regions comprises one or more reagents configured to react with one or more substances that may be present in said urine, and
wherein said test matrix further comprises at least one test region from said plurality of test regions comprising a colorimetric test, and immobilized active reagents configured to interact with at least one analyte in said urine, such that when an amount of said at least one analyte is present in said urine said at least one test region is configured to change in color with an intensity, and said change in color or said intensity of said change in color is configured to indicate whether said at least one analyte is present and in what quantities said at least one analyte is present;

a fluid transport system coupled to said urine collector and to said test chamber, and configured to transport a urine sample from said urine collector, and to dispense at least a portion of said urine sample onto each test region of the test matrix in said test chamber;

an optical sensor system within or proximal to said test chamber and configured to capture one or more signals from said test matrix in said test chamber after said one or more reagents have been exposed to said at least a portion of said urine sample;

a signal analyzer coupled to said optical sensor system and configured to receive said one or more signals from said test matrix; and, analyze said one or more signals from said test matrix to determine test results;

a cleaning solution container configured to contain a cleaning solution and coupled to said fluid transport system; and a wireless communication interface;

wherein said controller is coupled to said fluid transport system, to said optical sensor system, and to said wireless communication interface and wherein said controller is further configured to control said fluid transport system, said optical sensor system, and said wireless communication interface.

2. The toilet based urine analysis system of claim 1 further comprising:

a test matrix storage chamber configured to contain a plurality of test matrices;

a waste chamber configured to contain used test matrices; and, a test matrix transport mechanism coupled to said controller and configured to transport a test matrix of said plurality of test matrices from said test matrix storage chamber to said test chamber, and to transport said test matrix from said test chamber to said waste chamber after testing.

3. The toilet based urine analysis system of claim 2 wherein said test matrix storage chamber is configured to contain at least 6 test matrices; and, said waste chamber configured to contain at least 6 used test matrices.

4. The toilet based urine analysis system of claim 1 wherein said controller is configured to activate said collector actuator to move said urine collector to said deployed position;

activate said test matrix transport system to move said test matrix from said test matrix storage chamber to said test chamber;

activate said fluid transport system to transport said urine sample from said urine collector, and to dispense at least a portion of said urine sample onto each test region of the test matrix in said test chamber;

activate said optical sensor system to capture said one or more signals from said test matrix in said test chamber;

activate said test matrix transport system to move said test matrix in said test chamber to said waste chamber; and, activate said fluid transport system to transport said cleaning solution from said cleaning solution container to said test chamber.

5. The toilet based urine analysis system of claim 1 wherein said housing is mounted to a side of said bowl of said toilet;

said urine collector is coupled to an arm that is coupled to a hinge coupled to said housing; and, said movement of said urine collector from said retracted position to said deployed position, and from said deployed position back to said retracted position comprises rotation of said arm around said hinge.

6. The toilet based urine analysis system of claim 1 wherein each test matrix of said plurality of test matrices further comprises a barcode.

7. The toilet based urine analysis system of claim 6 wherein said barcode identifies one or more of an expiration date;

tests performed by said plurality of test regions; and, test calibration data for said plurality of test regions.

8. The toilet based urine analysis system of claim 1 further comprising:

a user control coupled to said controller and configured to send a command to said controller to initiate movement of said urine collector from said retracted position to said deployed position.

9. The toilet based urine analysis system of claim 8 wherein said user control comprises a button coupled to said controller.

10. The toilet based urine analysis system of claim 9 wherein said button is coupled to said controller via said wireless communication interface.

11. The toilet based urine analysis system of claim 8 wherein said user control comprises a control on an application configured to execute on a computer, mobile device or handheld device coupled to said controller via said wireless communication interface.

12. The toilet based urine analysis system of claim 1 further comprising:

an application configured to execute on a mobile device and configured to receive said test results from said signal analyzer; and, display said test results to said user.

13. The toilet based urine analysis system of claim 1 wherein said signal analyzer comprises a server coupled to said optical sensor system via one or more network connections.

14. The toilet based urine analysis system of claim 1 wherein said optical sensor system comprises one LED or a plurality of LEDs configured to emit a corresponding wavelength of light or a plurality of wavelengths of light.

15. The toilet based urine analysis system of claim 1 wherein said test matrix comprises test regions for 5 or more different urine analysis tests.

16. The toilet based urine analysis system of claim 1 wherein said test matrix comprises test regions for 15 or more different urine analysis tests.

17. The toilet based urine analysis system of claim 1 wherein said test matrix comprises test regions for 30 or more different urine analysis tests.

18. The toilet based urine analysis system of claim 1 wherein said test matrix further comprises at least one test region comprising a lateral flow test.

19. The toilet based urine analysis system of claim 1 wherein said urine collector is coupled with said toilet.

20. The toilet based urine analysis system of claim 1 wherein said urine collector is integrated into said toilet.

21. The toilet based urine analysis system of claim 1 wherein said urine collector comprises a trough.

22. The toilet based urine analysis system of claim 21 further comprising lips or flanges extending from said trough.

23. The toilet based urine analysis system of claim 21 wherein said trough is configured to minimize urine splashing via said lips or flanges to capture said urine and direct said urine into said trough.

24. The toilet based urine analysis system of claim 1 further comprising a reel of test matrices comprising said test matrix.

25. The toilet based urine analysis system of claim 1 further comprising a recommendation engine configured to convert multi-point health data sets into dietary and lifestyle recommendations.

26. The toilet based urine analysis system of claim 1 wherein said test matrix is disposable and configured to be discarded after use.

* * * * *